United States Patent
Katsu et al.

(10) Patent No.: US 10,832,041 B2
(45) Date of Patent: Nov. 10, 2020

(54) INFORMATION PROCESSING APPARATUS, INFORMATION PROCESSING METHOD, AND PROGRAM FOR DETECTING A TARGET MOTION

(71) Applicant: SONY CORPORATION, Tokyo (JP)

(72) Inventors: Masanori Katsu, Tokyo (JP); Sota Matsuzawa, Tokyo (JP)

(73) Assignee: SONY CORPORATION, Tokyo (JP)

( * ) Notice: Subject to any disclaimer, the term of this patent is extended or adjusted under 35 U.S.C. 154(b) by 261 days.

(21) Appl. No.: 15/541,065

(22) PCT Filed: Jan. 27, 2016

(86) PCT No.: PCT/JP2016/052395
§ 371 (c)(1),
(2) Date: Jun. 30, 2017

(87) PCT Pub. No.: WO2016/143404
PCT Pub. Date: Sep. 15, 2016

(65) Prior Publication Data
US 2017/0357849 A1 Dec. 14, 2017

(30) Foreign Application Priority Data
Mar. 12, 2015 (JP) .................................. 2015-049677

(51) Int. Cl.
*G06K 9/00* (2006.01)
*G06Q 50/10* (2012.01)
(Continued)

(52) U.S. Cl.
CPC ......... *G06K 9/00355* (2013.01); *G06F 1/163* (2013.01); *G06F 1/1694* (2013.01);
(Continued)

(58) Field of Classification Search
None
See application file for complete search history.

(56) References Cited

U.S. PATENT DOCUMENTS

2012/0143358 A1* 6/2012 Adams .................... G06F 3/011
700/92
2014/0200847 A1* 7/2014 Singiresu ............. G01C 22/006
702/141
(Continued)

FOREIGN PATENT DOCUMENTS

| CN | 103914136 A | 7/2014 |
|---|---|---|
| EP | 2782046 A2 | 9/2014 |

(Continued)

OTHER PUBLICATIONS

Nov. 7, 2018, Partial European Search Report issued for related EP application No. 16761376.9.
(Continued)

*Primary Examiner* — Roy Y Yi
*Assistant Examiner* — Geoffrey T Evans
(74) *Attorney, Agent, or Firm* — Paratus Law Group, PLLC

(57) ABSTRACT

There is provided an information processing apparatus to detect various motions of a user and generate useful information utilizing the result, the information processing apparatus including: a motion detection unit configured to detect a series of motions of a user which are repetitive and nonperiodic; and an information generation unit configured to generate information related to the series of motions.

20 Claims, 23 Drawing Sheets

(51) Int. Cl.
  *G06Q 30/02*   (2012.01)
  *G06Q 50/22*   (2018.01)
  *G06F 3/01*    (2006.01)
  *G06F 1/16*    (2006.01)
  *G06F 3/0346*  (2013.01)
  *G06F 1/3234*  (2019.01)
  *G06F 3/038*   (2013.01)
  *G06F 3/03*    (2006.01)
  *G06F 21/31*   (2013.01)

(52) U.S. Cl.
  CPC ............ *G06F 1/325* (2013.01); *G06F 1/3259* (2013.01); *G06F 3/011* (2013.01); *G06F 3/017* (2013.01); *G06F 3/0321* (2013.01); *G06F 3/0346* (2013.01); *G06F 3/0383* (2013.01); *G06K 9/0053* (2013.01); *G06K 9/00335* (2013.01); *G06K 9/00348* (2013.01); *G06Q 30/02* (2013.01); *G06Q 50/10* (2013.01); *G06Q 50/22* (2013.01); *G06F 21/31* (2013.01)

(56) References Cited

U.S. PATENT DOCUMENTS

| | | | | |
|---|---|---|---|---|
| 2014/0377724 | A1* | 12/2014 | Hoover | G06K 9/00355 434/127 |
| 2015/0139484 | A1* | 5/2015 | Wu | G06K 9/00624 382/103 |
| 2016/0063734 | A1* | 3/2016 | Divakaran | G06K 9/6202 382/110 |

FOREIGN PATENT DOCUMENTS

| | | |
|---|---|---|
| JP | 2000-245713 | 9/2000 |
| JP | 2003-173375 | 6/2003 |
| JP | 2005-021450 | 1/2005 |
| JP | 2006-340776 | 12/2006 |
| JP | 2010-198595 | 9/2010 |
| JP | 2013-003649 | 1/2013 |
| WO | WO2014/083779 A1 | 6/2014 |

OTHER PUBLICATIONS

Feb. 11, 2019, European Search Report issued for related EP application No. 16761376.9.

Ouchi, et al., 'Healthcare Services Using a Wearable Device', IPSJ SIG Technical Reports, vol. 2007, No. 14, Feb. 22-23, 2007, pp. 29-36.

Cho, et al., 'Implementation of Context-Aware Telematics Services Using Agent Framework', IEICE Transactions on Information and Systems, Pt.1, vol. J88-D-I No. 9, Sep. 1, 2005, pp. 1448-1458.

Jul. 23, 2019, Chinese Office Action issued for related CN Application No. 201610124867.7.

Mar. 3, 2020, Japanese Office Action issued for related JP Application No. 2017-504902.

Jan. 3, 2020, Chinese Office Action issued for related CN Application No. 201610124867.7.

* cited by examiner

| BEFORE MEAL | SHOPPING | | |
|---|---|---|---|
| | COOKING | | |
| | PREPARATION | HAND WASHING | |
| | MENU DISPLAY | RECOMMENDATION DISPLAY | FOOD COMBINATION INSTRUCTION |
| | | | WARNING ON DIETARY RESTRICTIONS |
| | MENU SELECTION | PAST MEAL DATA DISPLAY | |
| | ORDER | | |

FIG. 23

| | | | | |
|---|---|---|---|---|
| DURING MEAL | MEAL SERVING | TIMING | INSTRUCTION FOR PREVENTING OVEREATING | |
| | EATING | | INSTRUCTION FOR EATING SPEED | |
| | | ORDER OF EATING | | |
| | | MANNER | | |
| | WHILE DOING XX | | WHILE WATCHING TELEVISION | |
| | | | WHILE LISTENING TO MUSIC | |
| | | | WHILE READING NEWSPAPER | |
| | | | WHILE WORKING | |
| | MEMORIES OF TRIPS AND ANNIVERSARIES | IMAGE | PICTURE | |
| | | | VIDEO | |
| | | CONVERSATION | | |
| | INFORMATION PRESENTATION THAT MAKES MEAL ENJOYABLE | PROVIDE TOPIC OF CONVERSATION | | |
| | | INFORMATION ON CONTENTS OF CONVERSATION | | |
| | | INFORMATION ON PARTNER WHO IS TAKING MEAL TOGETHER | | |
| | INFORMATION PRESENTATION THAT MAKES MEAL DELICIOUS | INFORMATION ON CONTENTS OF MEAL | PRODUCTION AREA OF FOOD MATERIALS | |
| | | | CHARACTERISTICS OF FOOD MATERIALS | |
| | | | BIT OF KNOWLEDGE CONCERNING COOKING | |
| | | | RECOMMENDED FOOD COMBINATION MENU | |
| | | INFORMATION ON PLACE WHERE MEAL IS TAKEN | HISTORY, TOPIC | |
| | | | POPULAR MENU | |
| | | | INFORMATION ON SURROUNDING AREA | |

FIG. 24

| | | | |
|---|---|---|---|
| AFTER MEAL | COMMENTS ON MEAL | BLOG | |
| | | REVIEW | |
| | | SHARING | |
| | DIETARY MANAGEMENT | INSTRUCTION FOR CONTENTS OF MEAL | CALCULATION OF CALORIC INTAKE |
| | | | CALCULATION OF NUTRITION INTAKE |
| | HEALTH MANAGEMENT | EXERCISE INSTRUCTION | CALCULATION OF CALORIC CONSUMPTION |
| | | ALARM FOR PREVENTING FAILURE TO TAKE MEDICINE | |
| | AFTER-MEAL ACTION | SCHEDULE | |
| | | ToDo | |
| | | ENTERTAINMENT | |

INFORMATION PROCESSING APPARATUS, INFORMATION PROCESSING METHOD, AND PROGRAM FOR DETECTING A TARGET MOTION

CROSS REFERENCE TO PRIOR APPLICATION

This application is a National Stage Patent Application of PCT International Patent Application No. PCT/JP2016/052395 (filed on Jan. 27, 2016) under 35 U.S.C. § 371, which claims priority to Japanese Patent Application No. 2015-049677 (filed on Mar. 12, 2015), which are all hereby incorporated by reference in their entirety.

TECHNICAL FIELD

The present disclosure relates to an information processing apparatus, an information processing method, and a program.

BACKGROUND ART

In recent years, a technology has been proposed in which a motional action of a user is recognized from sensor information obtained using various sensing technologies. For example, Patent Literature 1 proposes an expression technique for presenting an action log recorded by a compact sensor built-in recording device to a user in an easy-to-understand manner utilizing such a technology.

CITATION LIST

Patent Literature

Patent Literature 1: JP 2013-3649A

DISCLOSURE OF INVENTION

Technical Problem

The technology as described in the Patent Literature 1 above also intends that a user continuously wears a sensor device and various actions occurring in his/her life, for example, are detected on the basis of sensor data. However, with further progress of size reduction and power saving of sensors, the sensors can be mounted on variously-shaped wearable devices, such as wrist wears, neck wears, and eye wears, for example, and accordingly, sources such as sensor data that can be utilized for detecting a motion of a user have been diversified. Meanwhile, it is considered that a technology for detecting a motion of a user and generating a information utilizing the result, including sensor data already utilized, still has potential for improvement.

Therefore, the present disclosure proposes an information processing apparatus, an information processing method, and a program being novel and improved that allow various motions of a user to be detected and useful information to be generated utilizing the result.

Solution to Problem

According to the present disclosure, there is provided an information processing apparatus including: a motion detection unit configured to detect a series of motions of a user which are repetitive and nonperiodic; and an information generation unit configured to generate information related to the series of motions.

Further, according to the present disclosure, there is provided an information processing method including: detecting, by a processor, a series of motions of a user which are repetitive and nonperiodic; and generating information related to the series of motions.

Further, according to the present disclosure, there is provided a program for causing a computer to achieve: a function of detecting a series of motions of a user which are repetitive and nonperiodic: and a function of generating information related to the series of motions.

Advantageous Effects of Invention

As described above, according to the present disclosure, various motions of a user can be detected, and useful information can be generated utilizing the result.

Note that the effects described above are not necessarily limitative. With or in the place of the above effects, there may be achieved any one of the effects described in this specification or other effects that may be grasped from this specification.

BRIEF DESCRIPTION OF DRAWINGS

FIG. 23 is an illustration showing variations of information that may be provided in the case of detecting a motion of taking a meal in an embodiment of the present disclosure.

FIG. 24 is an illustration showing variations of information that may be provided in the case of detecting a motion of taking a meal in an embodiment of the present disclosure.

MODE(S) FOR CARRYING OUT THE INVENTION

Figure 1:
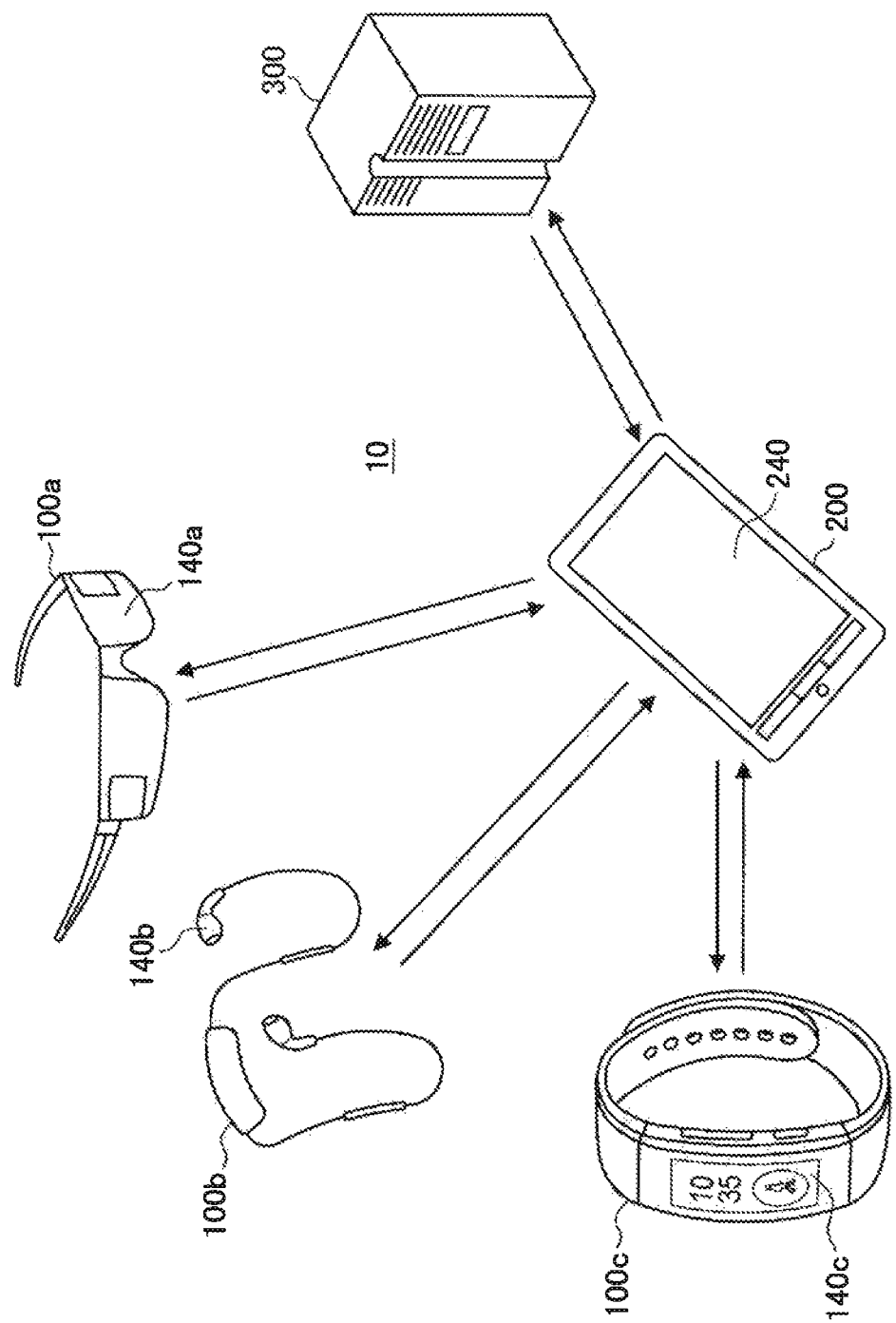
FIG. 1 is an illustration showing a schematic configuration of a system according to an embodiment of the present disclosure.

Hereinafter, (a) preferred embodiment(s) of the present disclosure will be described in detail with reference to the appended drawings, in this specification and the appended drawings, structural elements that have substantially the same function and structure are denoted with the same reference numerals, and repeated explanation of these structural elements is omitted.

Note that description will be provided in the following order.
1. System configuration
2. Functional configuration
2-1. Example of configuration for completion in a single device
2-2. Example of configuration for division among a plurality of devices
3. Examples of detected motions
4. Configuration in a case where there are a plurality of detection target motions
5. Examples of information generation
5-1. Examples of generating information before motion detection
5-2. Examples of generating information during motion detection
5-3. Examples of generating information after motion detection
5-4. Other examples
6. Hardware configuration
7. Supplement (1. System Configuration)

FIG. 1 is an illustration showing a schematic configuration of a system according to an embodiment of the present disclosure. Referring to FIG. 1, a system 10 includes a sensor device 100. As described later, the sensor device 100 also serves as an information processing apparatus, and may be capable of completing a sequential process inside the sensor device 100.

Moreover, the system 10 may include a terminal device 200 that communicates with the sensor device 100. More specifically, the terminal device 200 may be various types of information processing apparatuses, such as a smartphone, a tablet, or a personal computer, for example. The terminal device 200 executes a sequential process in cooperation with the sensor device 100. Note that in a case where a sequential process is completed inside the sensor device 100 as described above, the sensor device 100 and the terminal device 200 can also be regarded as being integral (a case where the sensor device 100 also serves as an information processing apparatus and a case where the terminal device 200 includes a sensor and also serves as a sensor device are equivalent).

Furthermore, the system 10 may include a server 300 that communicates with the terminal device 200 over a network. The server 300 is implemented by a single information processing apparatus or an assembly of a plurality of information processing apparatuses. In the case where the sensor device 100 and the terminal device 200 can be regarded as being integral as described above, it can also be said that the server 300 communicates with the sensor device 100. In addition, in a case where the sensor device 100 and the terminal device 200 exist separately, the server 300 may be capable of communicating with each of the sensor device 100 and the terminal device 200.

In the depicted example, the sensor device 100 is illustrated as an eye wear 100a, a neck wear 100b, and a wrist wear 100c. These wearable devices can be worn on the body of a user and can obtain sensor data, such as accelerations occurring to the body of the user. The sensor device 100 includes at least one sensor for obtaining such sensor data. More specifically, the sensor includes, for example, an acceleration sensor, a gyro sensor, a magnetic field sensor, an optical sensor, a sound sensor, a barometric sensor, and/or a position sensor (which may be implemented by, for example, a GNSS receiver, a Wi-Fi communication device, or the like). The sensor device 100 may process obtained sensor data internally. Alternatively, the sensor device 100 may transmit obtained sensor data to the terminal device 200. The sensor device 100 and the terminal device 200 execute wireless communication by Bluetooth (registered trademark) or Wi-Fi, for example.

In addition, the sensor device 100 may be provided with an output device for outputting information generated by internal processing or information generated by processing in the terminal device 200 or the server 300. In the depicted example, the eye wear 100a has a see-through display 140a as the output device. The see-through display 140a transparently superimposes an image on a real-space image that a user is visually recognizing. Moreover, the neck wear 100b has an earphone 140b as the output device. The wrist wear 100c has a display 140c as the output device. Note that the sensor device 100 may not necessarily be provided with an output device in such a case where an output device possessed by the terminal device 200 (a display 240 in the depicted example), for example, is available, or in a case where generated information is accumulated solely as a log and is not output in real time.

Furthermore, even in the case where the sensor device 100 has the output device, information generated by a sequential process according to the present embodiment may not be output from the output device.

Note that the sensor device 100 may be any of the eye wear 100*a*, the neck wear 100*b*, and the wrist wear 100*c* as depicted, or may be another type of wearable device. In addition, a mobile device, such as a smartphone, may serve as the sensor device 100. In this case, the mobile device may serve as both the sensor device 100 and the terminal device 200, or still another device may serve as the terminal device 200. Note that the sensor device 100 may be any one of wearable devices or mobile devices as described above, or a plurality of wearable devices and/or mobile devices may be included in the sensor device 100. In a case where the sensor device 100 is a single device, a plurality of pieces of sensor data may also be obtained by a plurality of sensors possessed by the device. These configurations may be utilized for obtaining a plurality of pieces of sensor data different in sensing target or sensing method, for example.

Among the structural elements of the system 10 as described above, one or a plurality of information processing apparatuses constituting the terminal device 200 and the server 300 are implemented by a hardware configuration of an information processing apparatus which will be described later, for example. It can also be said that the sensor device 100 is implemented by a hardware configuration of an information processing apparatus which will be described later since, not to mention the case where the sensor device 100 serves as an information processing apparatus to complete a sequential process, even otherwise, the sensor device 100 has a processing circuit (processor) that executes processing for transmitting obtained sensor data to the terminal device 200.

(2. Functional Configuration)
(2-1. Example of Configuration for Completion in a Single Device)

Figure 2:
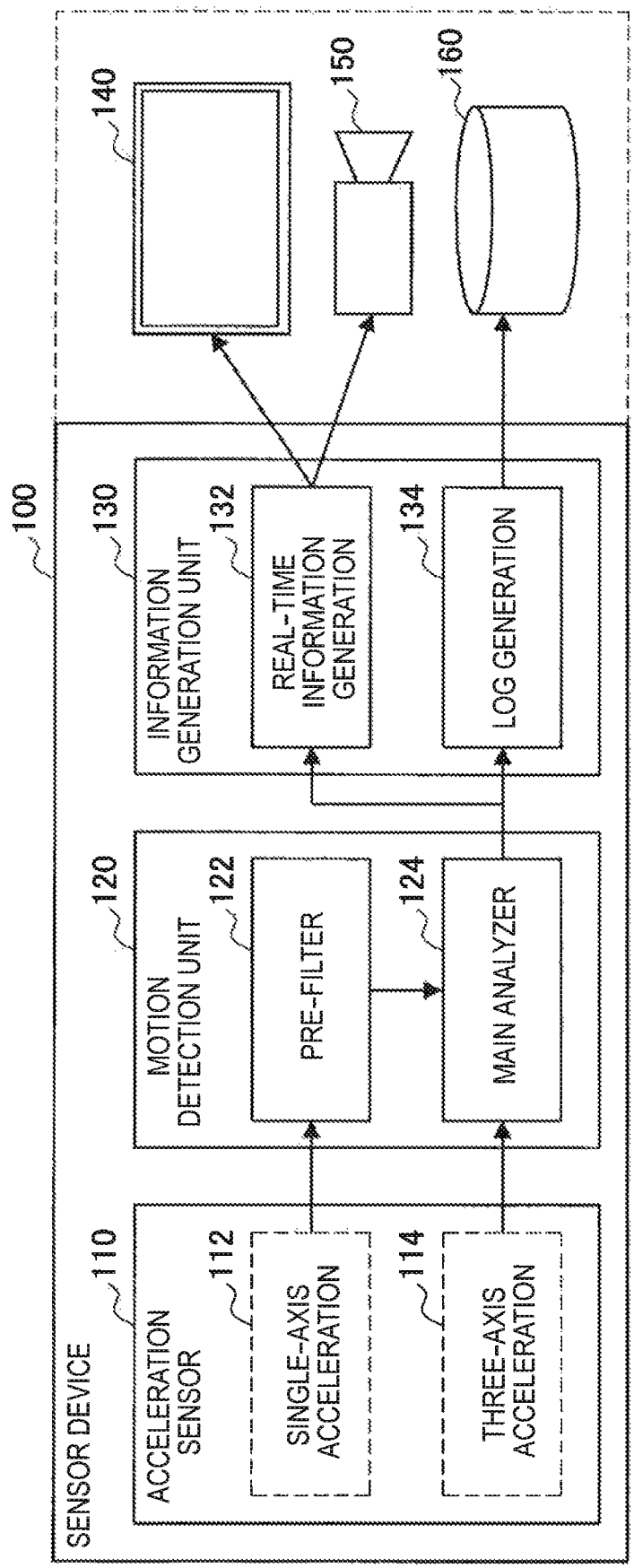
FIG. 2 is a block diagram showing an example of a functional configuration in a case where a sequential process is completed in a single device in an embodiment of the present disclosure.

FIG. 2 is a block diagram showing an example of a functional configuration in a case where a sequential process is completed in a single device in an embodiment of the present disclosure. In the example shown in FIG. 2, the sensor device 100 includes an acceleration sensor 110, a motion detection unit 120, and an information generation unit 130. The motion detection unit 120 and the information generation unit 130 are software-like structural elements implemented by a processor, such as CPU, for example, operating in accordance with a program. Hereinafter, the respective structural elements will be described further.

The acceleration sensor 110 is capable of obtaining sensor data on a single-axis acceleration 112 and a three-axis acceleration 114. The acceleration sensor 110 may include separate acceleration sensors for obtaining these pieces of sensor data (that is, a single-axis acceleration sensor and a three-axis acceleration sensor), or may obtain each piece of the above-described sensor data by changing the sensing method (including preprocessing of data output from an acceleration sensor) by the same acceleration sensor. Note that the acceleration sensor is described as an example of a sensor for obtaining sensor data for detecting a motion of a user, and a gyro sensor, a magnetic field sensor, an optical sensor, a sound sensor, a barometric sensor, and/or a position sensor, for example, may be used in combination, or the acceleration sensor 110 may be replaced by these sensors.

The motion detection unit 120 detects a motion of a user on the basis of sensor data provided from the acceleration sensor 110. In the depicted example, the sensor data provided from the acceleration sensor 110 includes sensor data on the single-axis acceleration 112 and the three-axis acceleration 114. As described above, these pieces of sensor data are exemplary multiple pieces of sensor data different in sensing target (in the case where the acceleration sensor 110 includes a single-axis acceleration sensor and a three-axis acceleration sensor separately) or different in sensing method (in the case where the acceleration sensor 110 obtains sensor data on the single-axis acceleration and the three-axis acceleration by changing the sensing method of the same acceleration sensor). In the depicted example, sensor data on the single-axis acceleration 112 (hereinafter, also referred to as first sensor data) is input to a pre-filter 122 (first motion detection unit) included in the motion detection unit 120, and sensor data on the three-axis acceleration 114 (hereinafter, also referred to as second sensor data) is input to a main analyzer 124 (second motion detection unit) included in the motion detection unit 120.

With such a configuration, in the motion detection unit 120, the pre-filter 122 can determine whether a section in which the first sensor data satisfies a first condition corresponding to a detection target motion has occurred, and in a case where it is determined that such a section has occurred, the main analyzer 124 can determine whether the second sensor data satisfies a second condition corresponding to the detection target motion in that section. Therefore, until it is determined by the pre-filter 122 that a section in which the first condition is satisfied has occurred, for example, processing in the main analyzer 124 and processing in which the acceleration sensor 110 provides the main analyzer 124 with sensor data on the three-axis acceleration 114 can be suspended. This can save consumption power of the processor that implements the motion detection unit 120, for example. Moreover, consumption power in the acceleration sensor 110 can also be saved by suspending the three-axis acceleration sensor in the case where the acceleration sensor 110 includes the single-axis acceleration sensor and the three-axis acceleration sensor separately, for example, or suspending a processing circuit for the acceleration sensor 110 to extract a three-axis acceleration from data output by an acceleration sensor (which is common to the single-axis acceleration and the three-axis acceleration).

In the present embodiment, the motion detection unit 120 detects a series of repetitive and nonperiodic motions of a user, such as taking a meal, billiards, typing, shopping, and soccer which will be described later, for example. Here, a series of repetitive motions of a user includes periodic motions, such as walking and running, for example, and other nonperiodic motions. The motion detection unit 120 may be capable of detecting periodic motions together with or instead of nonperiodic motions as described above. In addition, the motion detection unit 120 may be capable of detecting nonrepetitive temporary motions. Note that since publicly-known various techniques described in documents, such as JP 2013-3649A, for example, can be utilized as necessary for detection of such motions (nonrepetitive, or repetitive but periodic motions), detailed description is omitted here.

The information generation unit 130 generates information related to a motion detected by the motion detection unit 120 (which may include a series of repetitive and nonperiodic motions of the user). In the depicted example, the information generation unit 130 executes processing in a real-time information generation unit 132 and a log generation unit 134. The real-time information generation unit 132 generates information in accordance with an before-after relation with the detected motion. The information generated by the real-time information generation unit 132 may include information output via an output device 140, such as a display, for example. More specifically, such information may be recommended information or reminder information concerning an action of a user. In addition, the information generated by the real-time information generation unit 132 may include control information for a controlled device 150, such as a camera, for example. More specifically, the control information may include control information that causes a recording device, such as a camera, included in the controlled device 150 to execute recording. On the other hand, the Jog generation unit 134 generates log information after motion detection. The log information is accumulated in a database 160, for example, and is used for later analysis and output.

Note that the information generation unit 130 may generate any type of information in the above-described example, for example, or may generate a plurality of types of information. Therefore, processing in the information generation unit 130 may include both the real-time information generation unit 132 and the log generation unit 134, or may include either of them. Moreover, the information generated by the information generation unit 130 is not limited to the above-described example, hut may be any type of information as long as, by generating the information on the premise of occurrence of a motion during motion detection or after detection, more appropriate information can be provided for a user. Furthermore, together with or instead of the information as described above, the information generation unit 130 may generate another type of information that utilizes a detection result of a motion by the motion detection unit 120 but is not necessarily premised on occurrence of the motion.

In addition, in FIG. 2, the output device 140, the controlled device 150, and the database 160 which are output destinations of information generated by the information generation unit 130 are depicted in a manner that may be included in the sensor device 100, or may be external to the sensor device 100. This means that these output destinations may be a display, a camera, a storage, and the like possessed by the sensor device 100, for example, or may be a display, a camera, a storage, and the like possessed by the terminal device 200, for example, external to the sensor device 100. Note that the database 160 is not limited to the terminal device 200, but may be implemented by a storage of the server 300. In a case where information generated by the information generation unit 130 is output to the outside of the sensor device 100, the generated information is transmitted from a communication device possessed by the sensor device 100 to the terminal device 200 through wireless communication by Bluetooth (registered trademark) or Wi-Fi, for example. The terminal device 200 may transfer the received information to the server 300 through network communication. Alternatively, the generated information may be transmitted from the communication device possessed by the sensor device 100 directly to the server 300 through network communication.

Figure 3:
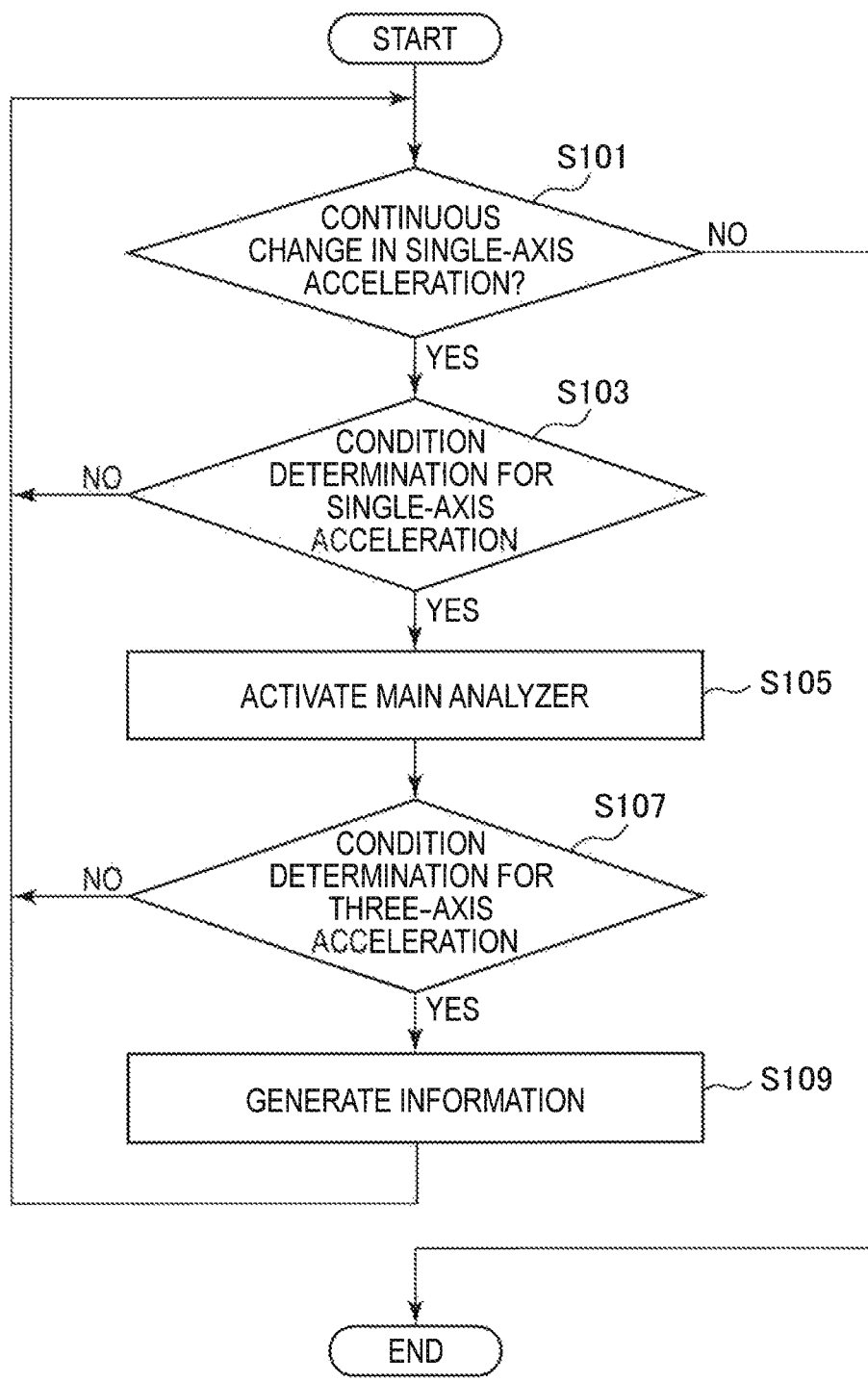
FIG. 3 is a flowchart showing an example of the process in the example shown in FIG. 2.

FIG. 3 is a flowchart showing an example of the process in the example shown in FIG. 2. FIG. 3 shows a process executed mainly by the motion detection unit 120 and the information generation unit 130 of the sensor device 100.

First, in the motion detection unit 120, the pre-filter 122 determines whether a continuous change in single-axis acceleration has been monitored in sensor data on the single-axis acceleration 112 provided from the acceleration sensor 110 (S101). Here, in a case where a continuous change in single-axis acceleration has not been monitored (NO), the process is terminated once, and executed again after the lapse of a predetermined time period, for example. On the other hand, in a case where a continuous change in single-axis acceleration has been monitored (YES), the pre-filter 122 carries out a condition determination for the single-axis acceleration (S103). This determination corresponds to the above-described determination as to whether a section in which the first sensor data satisfies the first condition corresponding to a detection target motion has occurred.

The first condition used in the above-described determination may be a condition that expresses as broadly as possible characteristics of the first sensor data (in the depicted example, the single-axis acceleration) that can be monitored in a case where a target motion has occurred, for example. As described later, whether a target motion has occurred is finally determined by the main analyzer 124. Therefore, in the determination by the pre-filter 122, if it is determined that the first condition is satisfied with high accuracy for a section in which a target motion has occurred actually, there is no problem if it is determined accordingly that the first condition is also satisfied in a portion of a section in which the target motion has not occurred actually. Thus, the determination processing for the first condition executed by the pre-filter 122 can be lighter processing that enables improvement in processing speed and saving of consumption power.

In the case where it is determined in the determination in S103 that the first condition is satisfied (YES), the main analyzer 124 is activated in the motion detection unit 120 (S105). At this time, an acceleration sensor included in the acceleration sensor 110 or a processing circuit for obtaining sensor data on the three-axis acceleration using a sensor may be activated together. The main analyzer 124 carries out a condition determination for the three-axis acceleration using sensor data on the three-axis acceleration 114 provided from the acceleration sensor 110 (S107). This determination corresponds to the above-mentioned determination as to whether the second sensor data satisfies the second condition corresponding to a detection target motion.

The second condition used in the above-described determination may be a condition that expresses as broadly as possible characteristics of the second sensor data that can be monitored in a case where a target motion occurs (in the depicted example, the three-axis acceleration), for example. Since the main analyzer 124 finally determines whether a target motion has occurred, it is desirable that a section for which it is determined that the second condition is satisfied is as close as possible to the section in which the target motion actually occurs. Thus, the determination processing for the second condition executed by the main analyzer 124 may be complicated processing accompanied by reduction in processing speed and increase in consumption power as long as the above-described object is achieved. Even in such a case, since at least a portion of a section in which the target motion has not occurred is filtered out from a processing target by the pre-filter 122, reduction in processing speed and increase in consumption power can be suppressed as compared with such a case of carrying out the determination for the second condition for all the sections, for example.

In a case where it is determined in the determination in S107 that the second condition is satisfied (YES), information generation by the information generation unit 130 is executed (S109). As already described, generated information may include some recommended information or reminder information regarding an action of a user output via the output device 140, control information for the controlled device 150, such as a camera, log information to be accumulated in the database 160, and the like.

After information generation, the motion-related determination processing in and subsequent to S101 described above is executed again. In a case where it is also determined that the target motion is occurring in the determination processing executed again (YES in S107), information may be generated in the information generation processing (S109) on the premise that the target motion is continuing. In addition, although not depicted, in a case where it is determined that the target motion is not occurring in the determination processing executed again (NO in S101, S103, or S107), information generation on the premise that the target motion has been terminated may be executed by the information generation unit 130.

An example of the configuration in the case where a sequential process is completed inside the sensor device in an embodiment of the present disclosure has been described above. Note that, as already described regarding the system configuration, a sequential process may be completed inside the terminal device 200 integrated with the sensor device 100. In this case, the sensor device 100 is replaced by the terminal device 200 in the above description. In this case, the terminal device 200 may be provided with the acceleration sensor 110 (or may be another type sensor) as described above to obtain sensor data by itself, and may receive sensor data from another sensor device through wireless communication or the like. A configuration in which the terminal device 200 receives sensor data from the sensor device 100 will be described further in the next example.

(2-2. Example of Configuration for Division Among a Plurality of Devices)

Figure 4:
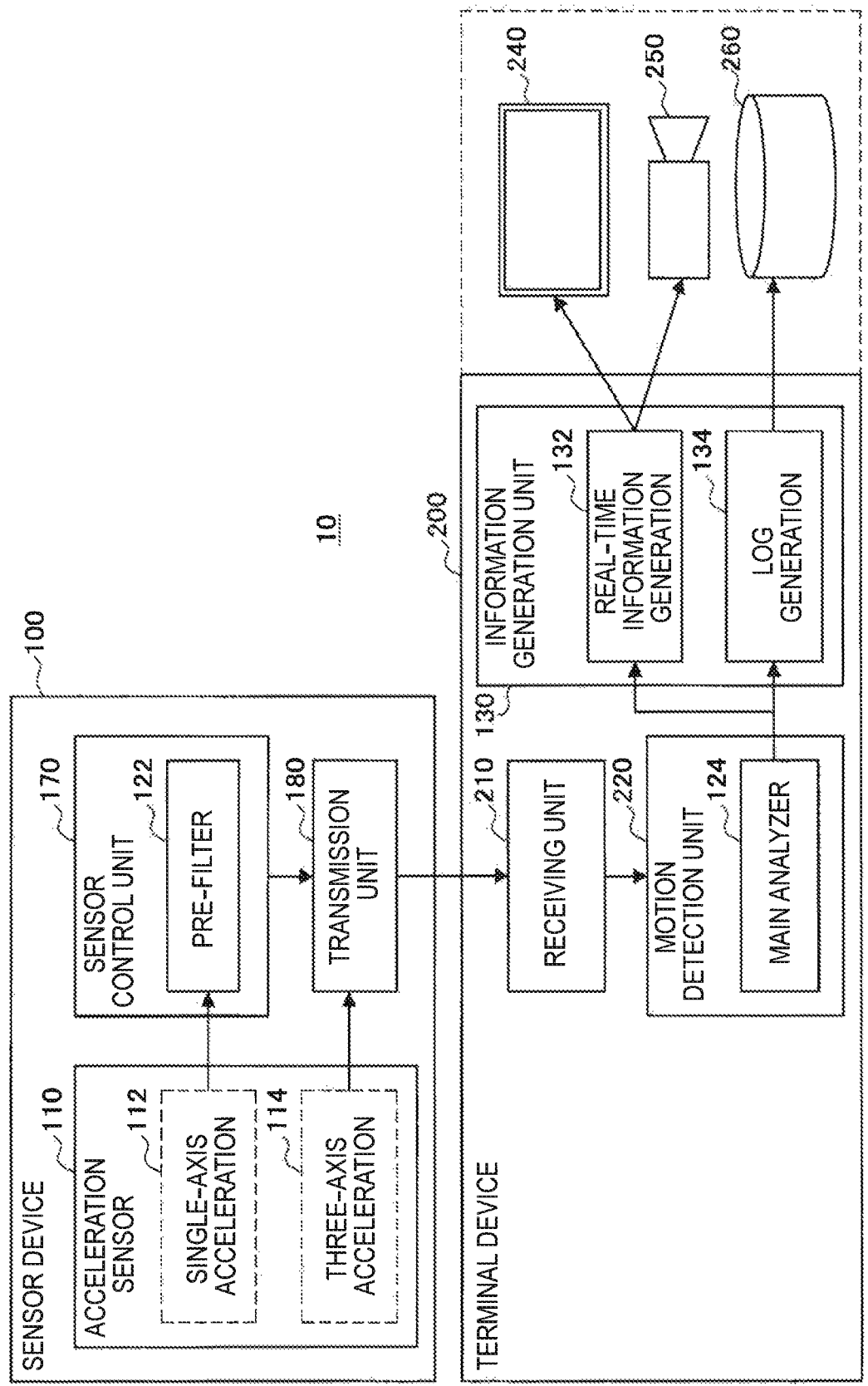
FIG. 4 is a block diagram showing an example of a functional configuration in a case where a sequential process is divided among and executed by a plurality of devices in an embodiment of the present disclosure.

FIG. 4 is a block diagram showing an example of a functional configuration in a case where a sequential process is divided among and executed by a plurality of devices in an embodiment of the present disclosure. Note that structural elements similar to the example described above with reference to FIG. 2 and FIG. 3 are denoted with common reference numerals, and thus, repeated description is omitted.

In the depicted example, the sensor device 100 includes the acceleration sensor 110, a sensor control unit 170, and a transmission unit 180. The sensor control unit 170 is a software-like structural element implemented by a processor, such as CPU, for example (which may be a simpler processing circuit), operating in accordance with a program. The transmission unit 180 is implemented by a communication device possessed by the sensor device 100 that executes wireless communication with the terminal device 200 by Bluetooth (registered trademark) or Wi-Fi.

The sensor control unit 170 controls an operation of the transmission unit 180 on the basis of sensor data provided from the acceleration sensor 110. More specifically, the sensor control unit 170 includes the pre-filter 122, and in a case where it is determined in the determination processing executed by the pre-filter 122 for sensor data on the single-axis acceleration 112 provided from the acceleration sensor 110 that a section in which the single-axis acceleration (first sensor data) satisfies the first condition corresponding to a detection target motion has occurred, the sensor control unit 170 activates the transmission unit 180. The activated transmission unit 180 transmits sensor data on the three-axis acceleration 114 provided from the acceleration sensor 110 to the terminal device 200. Until being activated, the transmission unit 180 may suspend communication with the terminal device 200. At this time, the sensor control unit 170 may further activate the three-axis acceleration sensor included in the acceleration sensor 110 or a processing circuit for obtaining sensor data on the three-axis acceleration using a sensor. Until being activated, these sensor or processing circuit may be suspended. Such a configuration can save consumption power of the communication device that implements the transmission unit 180 and consumption power in the acceleration sensor 110.

On the other hand, in the depicted example, the terminal device 200 includes a receiving unit 210, a motion detection unit 220, and the information generation unit 130. The receiving unit 210 is implemented by a communication device possessed by the terminal device 200 that executes wireless communication with the sensor device 100 by Bluetooth (registered trademark) or Wi-Fi. The motion detection unit 220 and the information generation unit 130 are software-like structural elements implemented by a processor, such as CPU, for example, operating in accordance with a program.

The receiving unit 210 receives sensor data transmitted from the sensor device 100. As described above, sensor data to be transmitted includes sensor data on the three-axis acceleration 114 provided from the acceleration sensor 110 possessed by the sensor device 100. As described above, the sensor device 100 transmits sensor data in the case where it is determined in the pre-filter 122 that a section in which the single-axis acceleration (first sensor data) satisfies the first condition corresponding to a detection target motion has occurred. Therefore, the receiving unit 210 will receive sensor data only in such a case. In a case where sensor data is received by the receiving unit 210, the main analyzer 124 is activated in the motion detection unit 220, and determination processing for sensor data on the three-axis acceleration 114 is executed. The determination processing executed here may be a determination as to whether the three-axis acceleration (second sensor data) satisfies the second condition corresponding to a detection target motion. While sensor data is not received by the receiving unit 210, the processing in the main analyzer 124 in the motion detection unit 220 is suspended. This can save consumption power of the processor that implements the motion detection unit 220, for example.

Similarly to the example described above with reference to FIG. 2 and FIG. 3, in the present embodiment, the motion detection unit 220 detects a series of repetitive and nonperiodic motions of the user. Note that the motion detection unit 220 may be capable of detecting periodic motions together with or instead of nonperiodic motions as described above. In addition, the motion detection unit 220 may be capable of detecting nonrepetitive temporary motions. Publicly-known various techniques can be utilized as necessary for detection of such motions, as already described.

In a case where a target motion (for example, a series of repetitive and nonperiodic motions of a user) is detected by the motion detection unit 220, the information generation unit 130 generates information during detection or after detection of the target motion on the premise of occurrence of the motion. Since a detailed configuration of the information generation unit 130 is similar to the example described above with reference to FIG. 2 and FIG. 3, detailed description is omitted.

Note that in the case of the information generation unit 130 included in the terminal device 200, output destinations of generated information are an output device 240, a controlled device 250, and/or a database 260. These output destinations are depicted in a manner that may be included in the terminal device 200, or may be external to the terminal device 200. This means that these output destinations may be a display, a camera, a storage, and the like possessed by the terminal device 200, for example, or may be a display, a camera, a storage, and the like possessed by another terminal device, for example (which may be the sensor device 100), external to the terminal device 200. Note that the database 260 may be implemented by the storage of the server 300. In a case where information generated by the information generation unit 130 is output to the outside of the terminal device 200, the generated information is transmitted from the communication device possessed by the sensor device 100 to another terminal device (which may be the sensor device 100) through wireless communication by Bluetooth (registered trademark) or Wi-Fi, for example. Alternatively, the generated information may be transmitted to the outside (another terminal device or the server 300) through network communication.

An example of the configuration in the case where a sequential process is divided among and executed by a plurality of devices in an embodiment of the present disclosure has been described above. In this case, a sequential process is divided between the sensor device 100 including the sensor control unit 170 (the pre-filter 122) and another device. Although the case where the process is divided between the sensor device 100 and the terminal device 200 has been described in the above example, the process may be divided between the sensor device 100 and the server 300. In this case, the server 300 includes the receiving unit 210, the motion detection unit 220, and the information generation unit 130 described above as structural elements of the terminal device 200. The terminal device 200 may relay transmission of sensor data from the sensor device 100 to the server 300. Alternatively, the sensor device 100 may directly transmit sensor data to the server 300 over a network.

Alternatively, in the above-described example, a sequential process may be divided among the sensor device 100 and other multiple devices. For example, the process may be divided among the sensor device 100, the terminal device 200, and the server 300, respectively. In this case, for example, the terminal device 200 may include the receiving unit 210 and the motion detection unit 220, and the server 300 may include the information generation unit 130. Alternatively, the information generation unit 130 may be mounted in a divided manner. More specifically, for example, the real-time information generation unit 132 may be executed in the terminal device 200, and the log generation unit 134 may be executed in the server 300.

As still another example, the sensor device 100 may not include the sensor control unit 170. In this case, the sensor device 100 transmits sensor data on the single-axis acceleration 112 and the three-axis acceleration 114 obtained in the acceleration sensor 110 to the terminal device 200 by the transmission unit 180. The terminal device 200 processes the sensor data received by the receiving unit 210 in the motion detection unit 220. In this case, the motion detection unit 220 may have a configuration similar to the motion detection unit 120 in the example shown in FIG. 2. That is, the motion detection unit 220 may include not only the main analyzer 124, but also the pre-filter 122. In this case, consumption power of the processor that implements the motion detection unit 220 in the terminal device 200 is saved although consumption power of the acceleration sensor 110 and the transmission unit 180 in the sensor device 100 is not saved. Here, in order to save consumption power in the sensor device 100 as well, the sensor control unit 170 may be included in the terminal device 200. In this case, the pre-filter 122 may be shared by the motion detection unit 220 and the sensor control unit 170. The terminal device 200 remotely controls the acceleration sensor 110 of the sensor device 100 via a communication device (which may be the same as the communication device that implements the receiving unit 210) in accordance with the determination result of the pre-filter 122 included in the sensor control unit 170.

(3. Examples of Detected Motions)

Next, examples of detected motions in an embodiment of the present disclosure will be described. As described above, in the present embodiment, the motion detection unit 120 (which may be the motion detection unit 220; the same applies hereinbelow) may be capable of detecting a series of repetitive and nonperiodic motions of a user (this is not necessarily so, but solely repetitive and periodic motions and/or nonrepetitive temporary motions may be detected as already described). A case where the motion detection unit 120 detects a series of repetitive and nonperiodic motions of a user will be further described below while citing some specific examples of the case.

Figure 5:
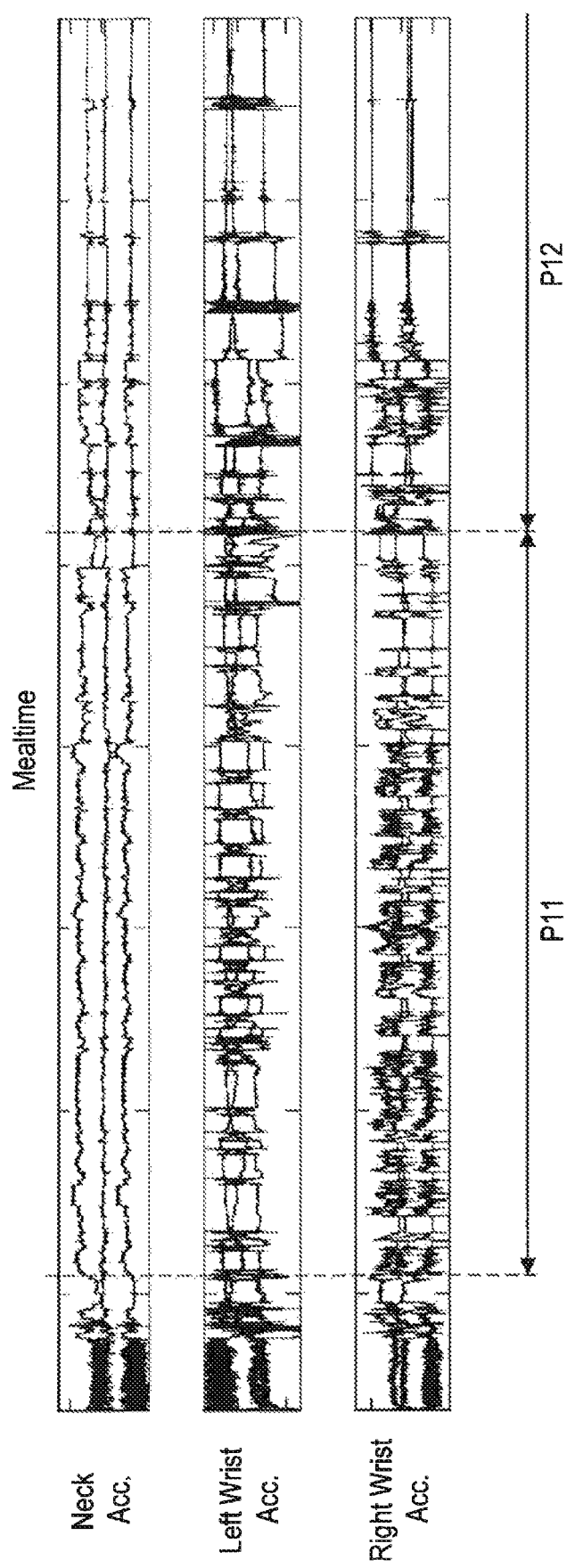
FIG. 5 is an illustration for describing an example of detecting a motion of taking a meal in an embodiment of the present disclosure.

FIG. 5 is an illustration for describing an example of detecting a motion of taking a meal in an embodiment of the present disclosure. FIG. 5 shows, regarding a section including a mealtime, waveforms of an acceleration (neck acceleration: NA) obtained by an acceleration sensor mounted on the neck of a user (for example, an acceleration sensor possessed by the neck wear 100b shown in FIG. 1) and accelerations (left wrist acceleration: LWA and right wrist acceleration: MA) obtained by acceleration sensors (tier example, acceleration sensors possessed by the wrist wear 100c shown in FIG. 1) respectively mounted on the left and right hands of the user. Among the depicted sections, a section P11 is a mealtime section, and a section P12 is an after-meal chat section.

In the present embodiment, in the case as described above, for example, a section in which a motion of taking a meal has occurred is detected on the basis of NA and MA. Note that in examples below (also including examples of detecting motions except a motion of taking a meal), LWA is merely used for detecting a motion section assuming that a right-handed user wears the wrist wear 100c on the wrist of the nondominant hand. Therefore, RWA may be used instead of LAVA in a case where, for example, the user wears the wrist wear 100c on the wrist of the dominant hand or the user is left-handed.

In line with the example described above with reference to FIG. 2 to FIG. 4, in this example, the pre-filter 122 of the motion detection unit 120 carries out a determination on the basis of sensor data on the single-axis acceleration 112 obtained by the acceleration sensor possessed by the neck wear 100b (three-axis accelerations are shown in FIG. 5, whilst a single-axis acceleration among them may be obtained). Moreover, the main analyzer 124 carries out a determination on the basis of sensor data on the three-axis acceleration 114 obtained by the acceleration sensor possessed by the wrist wear 100e. Determinators of the pre-filter 122 and the main analyzer 124 are generated by giving each sensor data in an actual mealtime section, for example, as teacher data to carry out machine learning. Alternatively, by analyzing movements of the neck and wrists of a user in a mealtime section (also using images and the like, for example), determinators may be generated on a rule basis.

In NA, characteristic waveforms in which detected values change little by little although the posture hardly changes are monitored in the section P11. Therefore, the pre-filter 122 can detect this section as a section in which the first condition corresponding to a meal is satisfied. Here, similar NA waveforms are monitored in a portion of the section P12. Therefore, at the stage of the pre-filter 122, not only the section P11, but also the portion of the section P12 may be detected as a section in which the first condition is satisfied.

The NA waveforms do not show characteristics as described above in the remaining portion of the section P12 and a section prior to the section P11, and thus can be filtered out from the target of the determination by the main analyzer 124 assuming that the condition corresponding to a meal is not satisfied at the time point in the pre-filter 122.

On the other hand, in LWA, there is a clear difference in waveform characteristics between the section P11 and the section P12. In the depicted example, while a user is taking a meal using chopsticks, waveforms corresponding to repetitive and nonperiodic motions of lifting a rice bowl toward the mouth by the left hand are monitored in a portion of the section P11 which is a mealtime section. On the other hand, such LWA waveforms are not monitored in the section P12 since the user is having a chat. Therefore, the main analyzer 124 can determine whether the second condition corresponding to a meal is satisfied on the basis of LWA in this section. Note that, regarding RWA, motions of holding chopsticks by the right hand and carrying food to the mouth have occurred, and they can also be regarded as repetitive and nonperiodic motions. Therefore, as described above, the mealtime section can also be detected using RWA instead of LWA in accordance with a state of wearing a sensor by the user or the like.

Figure 6:
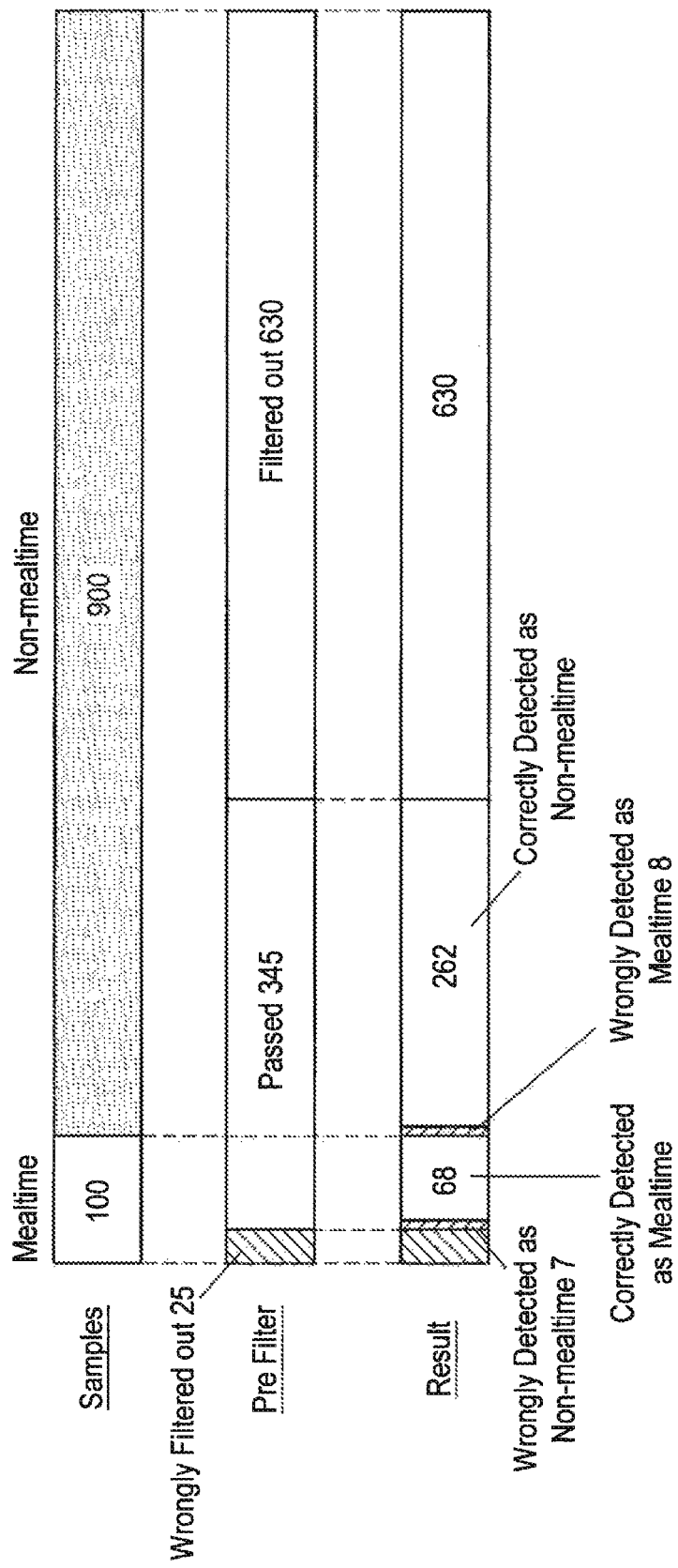
FIG. 6 is an illustration showing an experimental result on the example of detecting a motion of taking a meal in an embodiment of the present disclosure.

FIG. 6 is an illustration showing an experimental result for the example of detecting a motion of taking a meal in an embodiment of the present disclosure. In the experiments, regarding several tens of examples including the example shown in FIG. 5, sensor data in sections in which a user actually took meals and in other sections is collected in such a manner that actual mealtime sections and none mealtime sections appear in a ratio of 1:9. The user spent time wearing the neck wear 100*b* and the wrist wear 100*c*, and carried out input operations for recording the start point and end point of actual meals. In FIG. 6, determination results by each of the pre-filter 122 and the main analyzer 124 in the respective sections are shown by a ratio in a case of assuming the mealtime sections as 100 and the non-mealtime sections as 900. Note that determinators of the pre-filter 122 and the main analyzer 124 were generated by a technology described in JP 2010-198595A.

In the depicted results, first, in the determination in the pre-filter 122, 630/900 out of the non-mealtime sections were filtered out as sections in which the (meal) condition was not satisfied. On the other hand, 25/100 out of the actual mealtime sections were also filtered out (detection failures in the pre-filter 122). The remaining sections 345/1000 (including 75 mealtime sections and 270 non-mealtime sections) passed through the pre-filter 122.

Furthermore, in the determination (Result) in the main analyzer 124, 68/75 out of the actual mealtime sections having passed through the pre-filter 122 were determined as mealtime sections. Remaining 7/75 were detected as non-mealtime sections (detection failures in the main analyzer 124). However, considering that a relatively long interruption of a motion of taking a meal (for example, an interruption by a short conversation) may actually occur in a mealtime section, it is presumed that the sections described above as detection failures at least partly correspond to such interruption sections, and all of them cannot necessarily be regarded as total detection failures. On the other hand, 262/270 out of the actually non-mealtime sections having passed through the pre-filter 122 were determined as non-mealtime sections. Remaining 8/270 were detected as mealtime sections (erroneous detection).

In the above results, in a case of assuming the actual mealtime sections as 100%, a ratio in which actual mealtime sections were determined finally as mealtime sections (detection rate) was 68%, and a ratio in which actual mealtime sections were determined as non-mealtime sections (detection failure rate) was 32%. Out of them, the detection failures in the pre-filter 122 were 25%, and the detection failures in the main analyzer 124 were 7%. Moreover, a ratio in which actually non-mealtime sections were determined as mealtime sections in the motion detection unit 120 (erroneous detection rate) occurred in a ratio of 8 to 100 mealtime sections in the case where the ratio of mealtime sections and non-mealtime sections was 1:9.

In the above-described detection results, it is considered that the detection failures and erroneous detection occurred in the main analyzer 124 result from the accuracy of determinators and occurred even if the determination by the main analyzer 124 was carried out in all the sections. In contrast, the detection failures occurred in the pre-filter 122 (25% of actual mealtime sections) may not have occurred if the determination by the main analyzer 124 was carried out in all the sections without providing the pre-filter 122, and thus can be regarded as a disadvantage of carrying out the determination by the pre-filter 122. However, as described above, all of the sections described as detection failures are not necessarily total detection failures, but may correspond to sections of short interruptions of a motion of taking a meal, for example. Meanwhile, as an advantage of carrying out the determination by the pre-filter 122, the determination by the main analyzer 124 is omitted in 70% of actually non-mealtime sections, and corresponding consumption power and the like are saved. In order to interpolate these omissions, such processing of filling in the omissions in a portion where the omissions occur frequently may be arranged at the later stage.

In this manner, in the motion detection utilizing the pre-filter 122 and the main analyzer 124 in the present embodiment, detection failures caused by providing the pre-filter 122 (25% of actual mealtime sections in the example of FIG. 6) may occur, while in many sections (70% of actually non-mealtime sections in the example of FIG. 6), the effect exerted by omitting the determination by the main analyzer 124 can also be obtained (note that the ratio of detection failures and the like vary-depending on the detection target motion, quality of sensor data, or the like). Therefore, the present embodiment is effective in such a case where, for example, detection failures caused by providing the pre-filter 122 do not occur, or occur to an allowable degree. In addition, the present embodiment may also be effective in such a case where detection of a target motion by a detection method other than the method described above is used in combination, and detection failures caused by providing the pre-filter 122 can be covered by another detection method.

Figure 7:
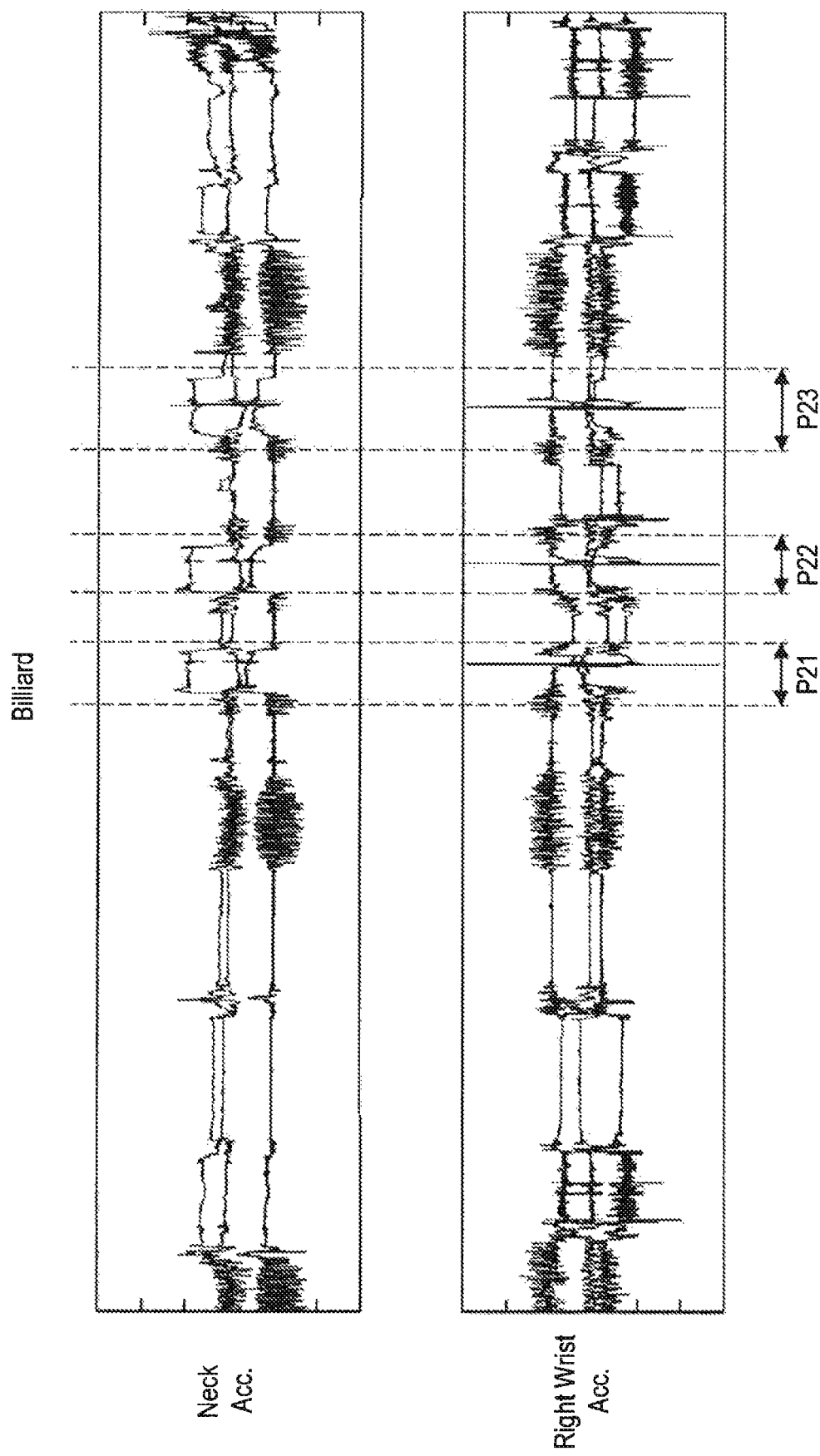
FIG. 7 is an illustration for describing an example of detecting a billiards play in an embodiment of the present disclosure.

FIG. 7 is an illustration for describing an example of detecting a billiards play in an embodiment of the present disclosure. FIG. 7 shows, regarding a section including a billiards play, waveforms of an acceleration (NA) obtained by an acceleration sensor mounted on the neck of a user and an acceleration (RWA) obtained by an acceleration sensor mounted on the right wrist (as described above, the wrist of the dominant hand) of the user (for about five minutes). Among the depicted sections, sections P21, P22, and P23 are sections including billiards shots. In this example, the pre-filter 122 of the motion detection unit 120 carries out a determination on the basis of sensor data on NA obtained by an acceleration sensor possessed by the neck wear 100*b*, for example. Moreover, the main analyzer 124 carries out a determination on the basis of sensor data on RWA obtained by an acceleration sensor possessed by the wrist wear 100*c*, for example.

In each of the sections P21, P22, and P23, characteristic waveforms resulting from the user staying still in a certain posture for giving shots (for the same user, variations among shots are small) are monitored in NA. Therefore, the pre-filter 122 can detect these sections as sections in which the first condition corresponding to a billiards shot is satisfied. Furthermore, in these sections, characteristic waveforms resulting from the user hitting with a cue stick by the right hand are monitored in RWA (although not shown, characteristic waveforms may also be monitored in LWA since the user supports the cue stick by the left hand). Therefore, the main analyzer 124 can execute a determination using characteristics of these waveforms as the second condition corresponding to a billiards shot. As a result, billiards play sections in which shots occur as repetitive and nonperiodic motions can be detected.

Figure 8:
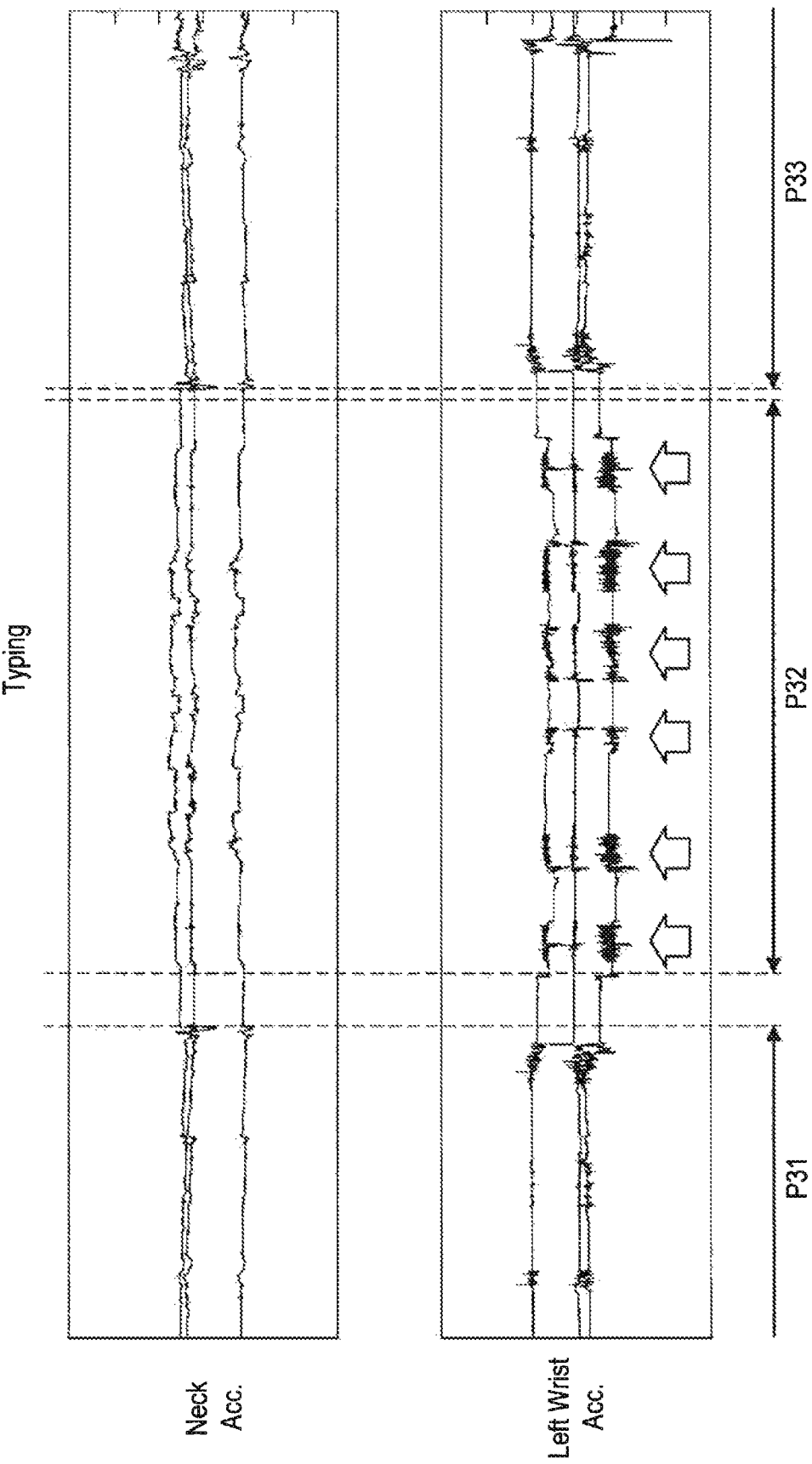
FIG. 8 is an illustration for describing an example of detecting typing in an embodiment of the present disclosure.

FIG. 8 is an illustration for describing an example of detecting typing in an embodiment of the present disclosure. FIG. 8 shows, regarding a section including typing, waveforms of an acceleration (NA) obtained by an acceleration sensor mounted on the neck of a user and an acceleration (LWA) obtained by an acceleration sensor mounted on the left wrist of the user (for about five minutes). Among the depicted sections, a section P32 is a typing section. A section P31 and a section P33 are sections in which the user performed writing in a notebook. In this example, the pre-filter 122 of the motion detection unit 120 carries out a determination on the basis of sensor data on NA obtained by an acceleration sensor possessed by the neck wear 100*b*, for example. Moreover, the main analyzer 124 carries out a determination on the basis of sensor data on LWA obtained by an acceleration sensor possessed by the wrist wear 100*e*, for example.

In each of the sections P31, P32, and P33, changes in NA are small since the user is sitting at a table. Therefore, the pre-filter 122 can detect these sections as sections in which the first condition corresponding to typing is satisfied. Note that, outside the depicted range, there may be sections in which the user stands up from the table and walks around, for example. The pre-filter 122 can filter out such sections from the target of the determination by the main analyzer 124 as not satisfying the first condition as described above. On the other hand, in LWA, there is a clear difference in characteristics of waveforms between the section P32 and the sections P31 and P33. In the section P32 which is the typing section, repetitive and nonperiodic acceleration waveforms resulting from key strokes are monitored as indicated by arrows in the drawing. On the other hand, in the section P31 and the section P33, such LWA waveforms are not monitored since the user is only pressing the notebook by the left hand. Therefore, the main analyzer 124 can execute a determination using characteristics of such waveforms as the second condition corresponding to typing. Note that, regarding RWA, waveforms similar to LWA may also be monitored in the section P32, while the user performs writing holding a pen by the right hand in the section P31 and the section P33, and thus in RWA, repetitive and nonperiodic acceleration waveforms are also monitored in these sections, and a difference from the section P32 is not clear. Therefore, in a case of using RWA for detecting typing, processing in the main analyzer 124 may be different from LWA.

Figure 9:
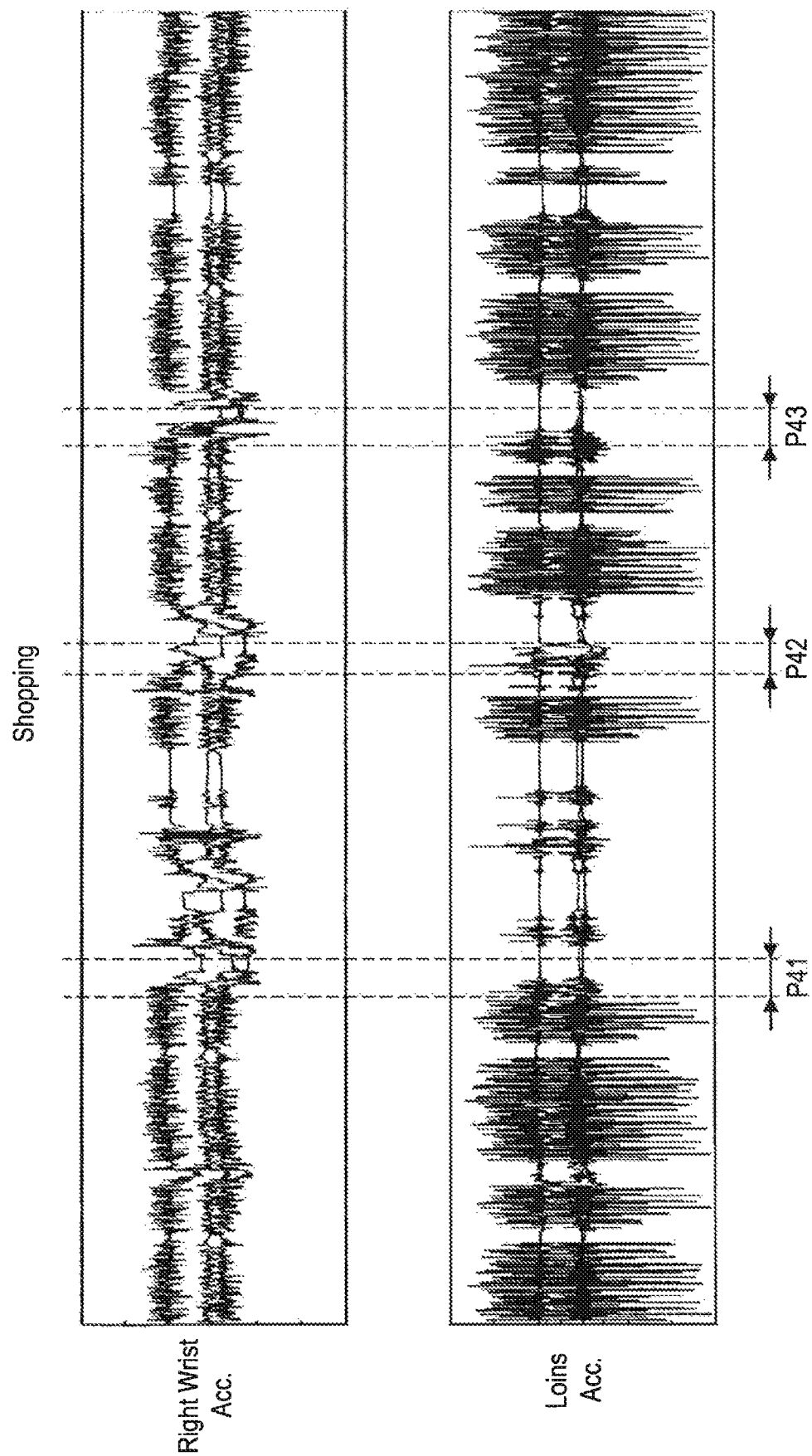
FIG. 9 is an illustration for describing an example of detecting shopping in an embodiment of the present disclosure.

FIG. 9 is an illustration for describing an example of detecting shopping in an embodiment of the present disclosure. FIG. 9 shows, regarding a section during shopping, waveforms of an acceleration (RWA) obtained by an acceleration sensor mounted on the right wrist of a user and an acceleration (loins acceleration: LA) obtained by an acceleration sensor mounted on the loins of the user (for about five minutes). Among the depicted sections, sections P41, P42, and P43 are sections in which the user performed motions of reaching for goods during shopping. In this example, the pre-filter 122 of the motion detection unit 120 carries out a determination on the basis of sensor data on LA obtained by an acceleration sensor possessed by a smartphone that serves as the sensor device 100 (which may also serve as the terminal device 200), for example. Moreover, the main analyzer 124 carries out a determination on the basis of sensor data on RWA obtained by an acceleration sensor possessed by the wrist wear 100*c*, for example.

In each of the section P41 and the section P43, characteristic waveforms resulting from the user stopping to reach for goods are monitored in LA. Therefore, the pre-filter 122 can detect these sections as sections in which the first condition corresponding to shopping is satisfied. On the other hand, in the section P42, characteristic waveforms resulting from the user not only stopping to reach for goods but also stooping down are monitored in LA. The pre-filter 122 may detect these sections as sections in which another first condition corresponding to shopping is satisfied. Alternatively, in the motion detection unit 120, labels showing different motions may be provided for these sections (the sections P41 and P43 and the section P42), and the pre-filter 122 may detect the respective sections as sections in which the first condition corresponding to the different motions is satisfied, respectively.

On the other hand, in each of the sections P41, P42, and P43, characteristic waveforms resulting from the user reaching for goods are monitored in RWA. Therefore, the main analyzer 124 can carry out a determination using characteristics of these waveforms as the second condition corresponding to shopping. At this time, a common main analyzer 124 may be used for the sections P41 and P43 (the sections in which the user stopped) and the section P42. (the section in which the user not only stopped but also stooped down), or different main analyzers 124 may be used respectively. As a result, shopping sections in which the motion of the user stopping and stooping down to reach for goods occurs repetitively and nonperiodically can be detected.

Figure 10:
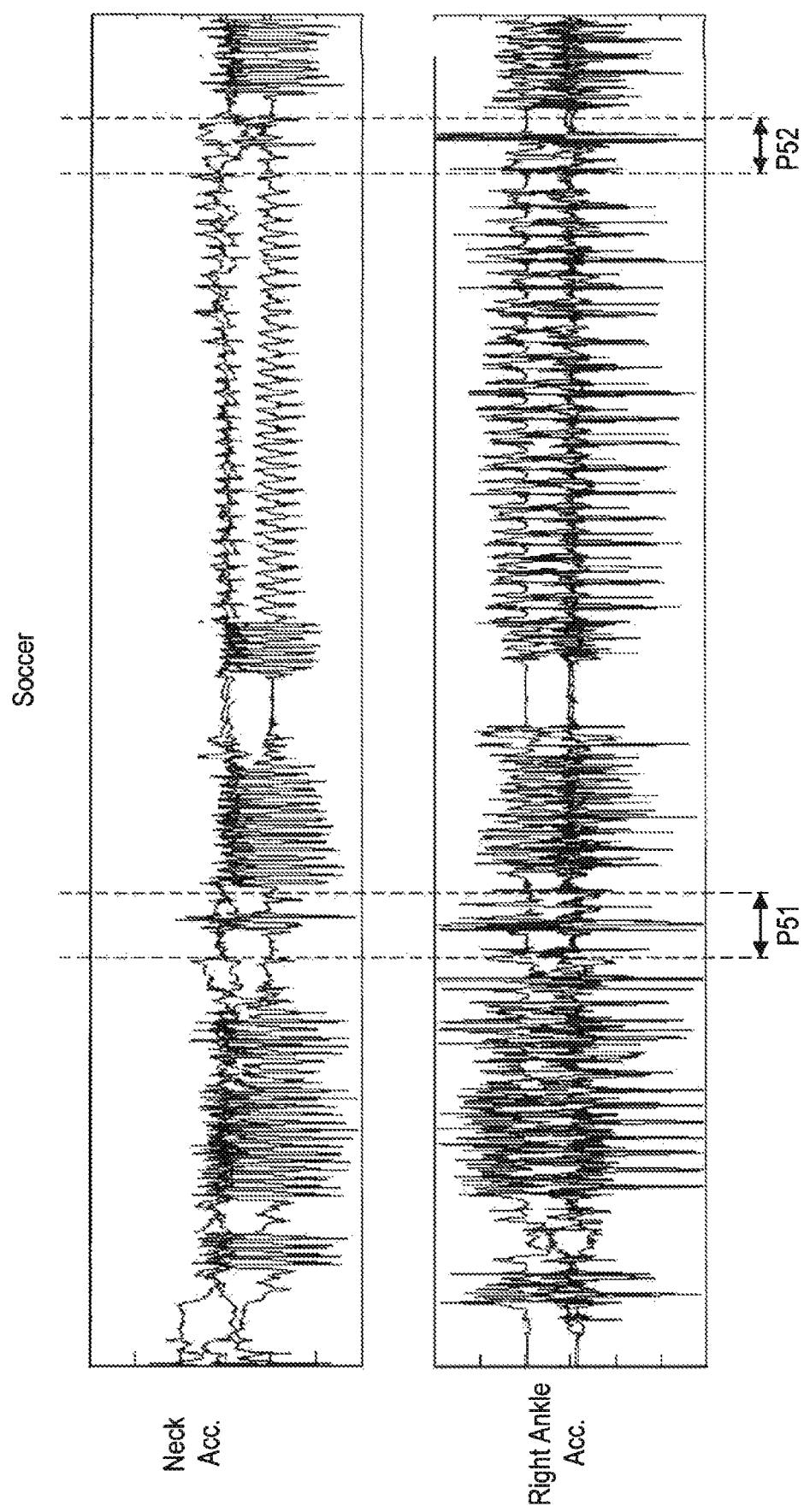
FIG. 10 is an illustration for describing an example of detecting a soccer play in an embodiment of the present disclosure.

FIG. 10 is an illustration for describing an example of detecting a soccer play in an embodiment of the present disclosure. FIG. 10 shows, regarding a period including a soccer play, waveforms of an acceleration (NA) obtained by an acceleration sensor mounted on the neck of a user and an acceleration (right ankle acceleration: RAA) obtained by an acceleration sensor mounted on the right ankle (the ankle of the dominant leg) of the user (for about 1 minute). Among the depicted sections, sections P51 and P52 are sections including soccer kicks. In this example, the pre-filter 122 of the motion detection unit 120 carries out a determination on the basis of sensor data on NA obtained by an acceleration sensor possessed by the neck wear 100*b*, for example. Moreover, the main analyzer 124 carries out a determination on the basis of sensor data on RAA obtained by an acceleration sensor possessed by a wearable device of the type mounted on the ankle, for example.

In each of the sections P51 and P52, characteristic waveforms resulting from the user performing kick motions are monitored in NA. Therefore, the pre-filter 122 can detect these sections as sections in which the first condition corresponding to a soccer kick is satisfied. Furthermore, in these sections, characteristic waveforms (impacts) resulting from the user kicking a ball are monitored in RAA. Therefore, the main analyzer 124 can execute a determination using characteristics of these waveforms as the second condition corresponding to a soccer kick. As a result, soccer play sections in which kicks occur as repetitive and nonperiodic motions can be detected.

A series of repetitive and nonperiodic motions of a user that may be detected in the present embodiment have been described above. In the present embodiment, the motion detection unit 120 may collectively detect sections including a series of repetitive and nonperiodic motions as in the example of a meal shown in FIG. 5 and the example of typing shown in FIG. 8, for example (motions of using a fork by the left hand, keystrokes, and the like, for example). Alternatively, upon detection of each of sections of nonperiodic individual motions (for example, billiards shots, motions of reaching for goods, soccer kicks, etc.) as in the example of billiards shown in FIG. 7, the example of shopping shown in FIG. 9, and the example of soccer shown in FIG. 10, for example, the motion detection unit 120 may recognize sections in which such motions are repeated as sections of detection target motions (billiards plays, shopping, or soccer plays).

A series of repetitive and nonperiodic motions of a user recognized as described above are not limited to the illustrated motions, but many other motions may also occur in the daily life of the user. Since such motions are not periodic although being characteristic in that they are repetitive, there is a case where sections cannot be specified easily. In such a case, if sections in which motions could have occurred can be narrowed down to some degree on the basis of the determination by the pre-filter 122, for example, occurrence of a target motion can be detected accurately by the determination by the main analyzer 124. In addition, by executing the determination by the main analyzer 124 and obtaining sensor data for use in the determination only in the case where it is determined in the pre-filter 122 that the condition has been satisfied, consumption power and the like may be saved, as already described.

Note that in the case of detecting a series of repetitive and nonperiodic motions of a user in another embodiment of the present disclosure, the motion detection unit does not necessarily have a configuration that includes the pre-filter (first motion detection unit) and the main analyzer (second motion detection unit). For example, in a case where a pre-filter that appropriately narrows down sections in which a target motion could have occurred cannot be built easily, or in a case where saving of consumption power and the like by providing the pre-filter is not required, the motion detection unit may not include a pre-filter, and may carry out a determination by the main analyzer for all sections, That is, in an embodiment of the present disclosure, detecting a series of repetitive and nonperiodic motions is independent from providing the pre-filter and the main analyzer.

In addition, as already described, in the present embodiment, a series of repetitive and nonperiodic motions of a user may not necessarily be detected, but repetitive and periodic motions or nonrepetitive temporary motions may be detected instead. In cases of detecting such motions, it may also be possible to save consumption power and the like by the motion detection unit including the pre-filter and the main analyzer, similarly to the case of detecting repetitive and nonperiodic motions.

(4. Configuration in a Case where there are a Plurality of Detection Target Motions)

Figure 11:
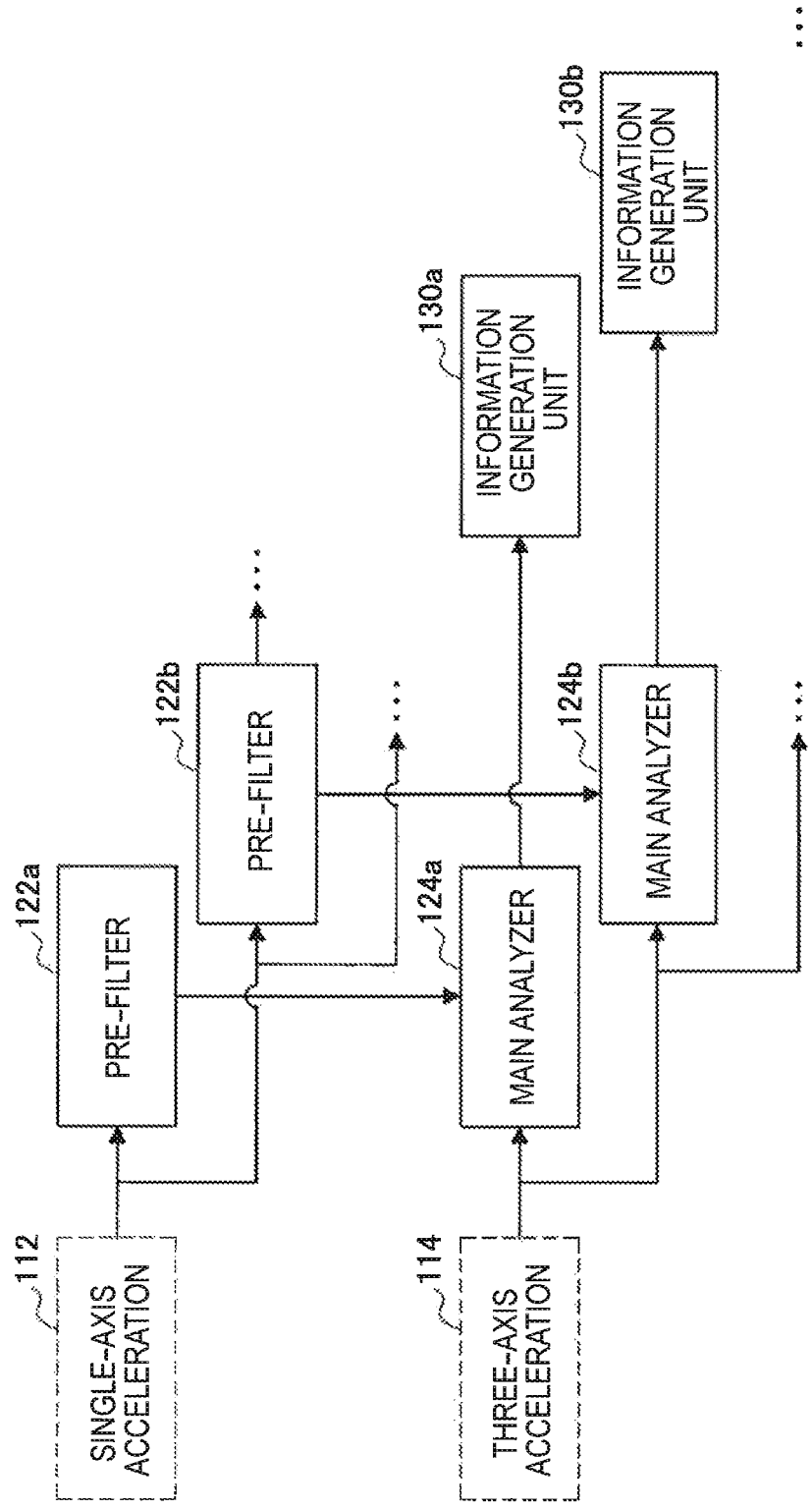
FIG. 11 is an illustration showing a first example of a configuration in a case where there are a plurality of detection target motions in an embodiment of the present disclosure.

FIG. 11 is an illustration showing a first example of a configuration in a case where there are a plurality of detection target motions in an embodiment of the present disclosure. In the present embodiment, it may be possible to detect each of a plurality of motions as in the examples above with reference to FIG. 5 to FIG. 10, for example. Moreover, for example, there may be cases where even motions provided with the same label may include a plurality of detection targets. For example, in the example of meal detection described with reference to FIG. 5, characteristics of each detected acceleration (for example, characteristics of LWA occurred by a left-hand motion) may differ among the manners of using tableware (a case of using a fork and a knife, a case of using a spoon, a case of using chopsticks, and the like). Furthermore, for example, characteristics of detected accelerations may differ among the types of food (rice, bread, noodles, soup, and the like). Therefore, in meal detection, for example, such detection targets may be integrated into one meal (the manner of using tableware may be changed during one meal, or a plurality of types of food may be taken sequentially or alternately).

In the depicted example, pre-filters 122a, 122b, . . . corresponding to respective detection target motions and main analyzers 124a, 124b, . . . similarly corresponding to respective detection target motions are provided. In addition, an information generation unit 130a corresponding to each detection target motion may be provided. Sensor data on the single-axis acceleration 112 is input to each of the pre-filters 122a, 122b, . . . , and sensor data on the three-axis acceleration 114 is input to each of the main analyzers 124a, 124b, . . . . A corresponding one of the main analyzers 124a, 124b . . . is activated in accordance with a determination result of the pre-filters 122a, 122b, . . . . More specifically, for example, in a case where it is determined in the pre-filter 122a that a section in which a condition corresponding to a first detection target motion is satisfied has occurred, the main analyzer 124a is activated. At this time, if it is not determined similarly in the pre-filter 122b that a section in which a condition corresponding to a second detection target motion is satisfied has occurred, the main analyzer 124b is not activated. For example, in a case where there is a great difference in characteristics of sensor data on the single-axis acceleration 112 among respective detection target motions, and the respective detection target motions can be identified by the pre-filters 122a, 122b, . . . , the configuration as described above may be effective.

Figure 12:
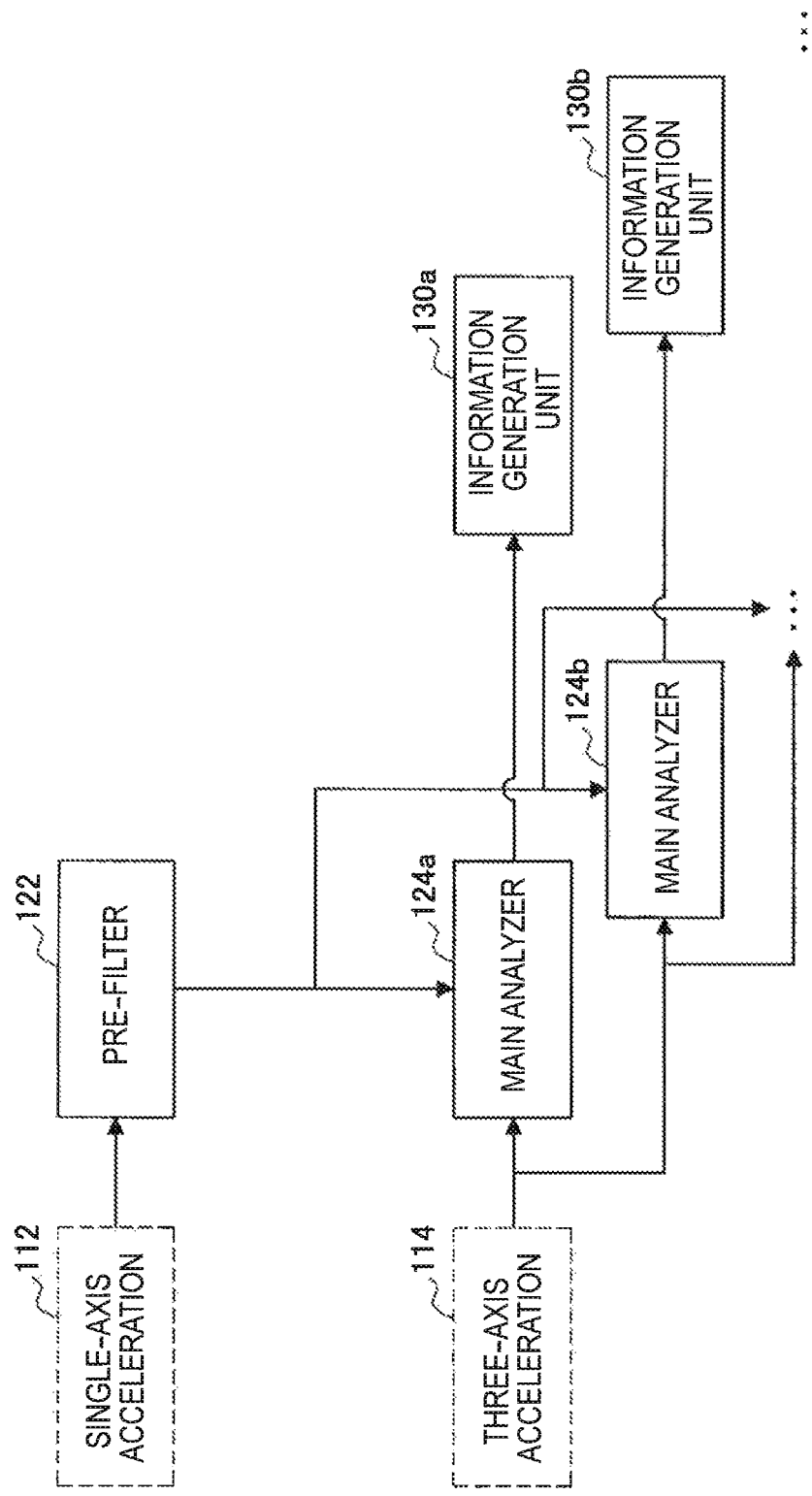
FIG. 12 is an illustration showing a second example of a configuration in a case where there are a plurality of detection target motions in an embodiment of the present disclosure.

FIG. 12 is an illustration showing a second example of a configuration in a case where there are a plurality of detection target motions in an embodiment of the present disclosure. In the depicted example, the pre-filter 122 common to a plurality of detection target motions and the main analyzers 124a, 124b, . . . corresponding to respective detection target motions are provided. Sensor data on the single-axis acceleration 112 is input to the pre-filter 122, and sensor data on the three-axis acceleration 114 is input to each of the main analyzers 124a, 124b, . . . The main analyzers 124a, 124b, . . . are activated in accordance with a determination result of the pre-filter 122. More specifically, for example, in a case where it is determined in the pre-filter 122 that a section in which a condition common to the respective detection target motions is satisfied has occurred, each of the main analyzers 124a, 124b, . . . is activated. For example, in a case where there is a small difference in characteristics of sensor data on the single-axis acceleration 112 among respective detection target motions, and it is not reasonable to identify the respective detection target motions in the pre-filter 122, the configuration as described above may be effective.

Examples of configurations concerning motion detection in an embodiment of the present disclosure have been described so far. The examples described here are not limitations, but various variations are available concerning motion detection in an embodiment of the present disclosure. For example, the sensor devices are not limited to an eyewear, a neckwear, and a wrist wear as in the above-described example, but may be worn on the arm, ankle, clothes, tooth, or the like of a user. Moreover, the sensor devices may not necessarily be worn by a user, but may be mounted on or built in a tool used by a user, for example, tableware used for a meal (edge, dish, or the like). Furthermore, sensor data included in the sensor devices and used for motion detection by the motion detection unit is not limited to sensor data on accelerations in the above-described example, but may be the angular velocity, geomagnetism, barometric pressure, or the like obtained by a gyro sensor. Sensor data may include image data obtained by an image sensor included in a camera or the like and audio data obtained by a microphone (sound sensor). In addition, sensor data may include position data obtained by a GNSS receiver, a Wi-Fi communication device, or the like (which can be regarded as a position sensor).

Here, regarding the combination of sensor data as described above, since the place where a meal can be taken is limited to home, restaurants, and the like in a case of detecting a motion of taking a meal, for example, the accuracy of detection may be improved by carrying out filtering based on position data. Points of interest (POI) personalized by, fir example, facilitating detection of a motion of taking a meal (facilitating passage through the pre-filter 122) for places where it has already been detected that a meal was taken may be utilized. Note that detecting a motion of taking a meal utilizing position data increases the accuracy of recognition, while dependence on position data may be a restraint in motion detection. For example, if parameters can be automatically adjusted by using a technology such as machine learning in the procedure of repeating detection of a motion of taking a meal using sensor data on accelerations together with position data, and the accuracy of determinators based on the accelerations can be improved sufficiently, a motion of taking a meal can be detected with sufficient accuracy even in a case where position data has not necessarily been obtained or cannot be obtained easily. Moreover, if a motion of taking a meal can be detected without depending on position data, whether the elderly who rarely leaves home (whose changes in position data between a time slot of a meal and other time slots are small), for example, has taken a meal, the contents of a meal, and the like can also be detected accurately.

Furthermore, for example, in a case where the motion detection unit 120 is capable of detecting other motions, for example, walking, running, and the like that are detected as periodic motions, a detection result of these other motions may be utilized for detection of a motion of taking a meal. More specifically, it may be set such that a motion of taking a meal is not detected while walking or running (which may include other movements) is detected since it is basically considered that a meal is not taken. Alternatively, a motion of taking a meal detected during walking may be regarded separately from a normal motion of taking a meal, and information that prompts to stop taking a meal during walking may be output since it is not a very good behavior to take a meal during walking or the like.

(5. Examples of Information Generation)
(5-1. Examples of Generating Information Before Motion Detection)

Figure 13:
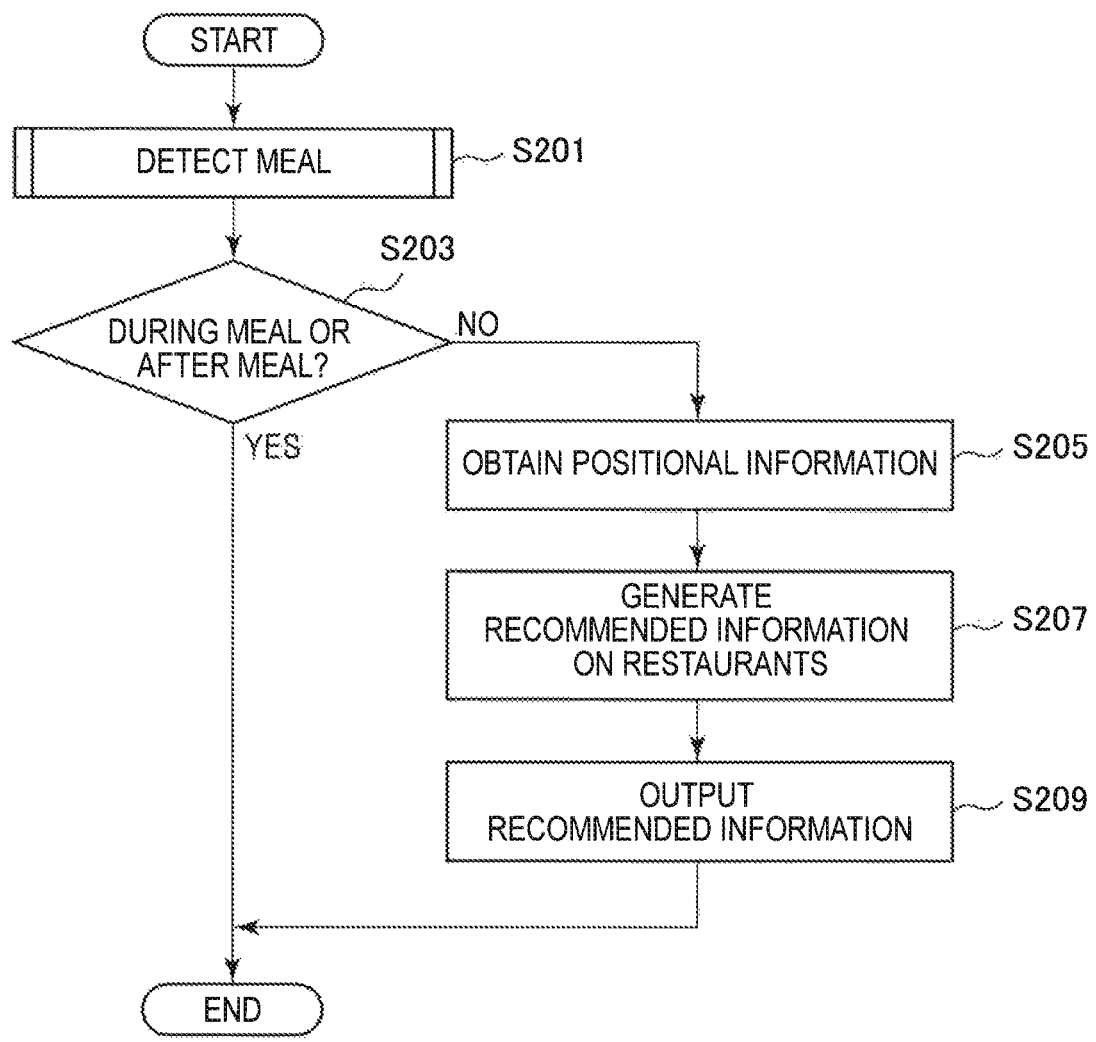
FIG. 13 is a flowchart showing an example of generating information before motion detection in an embodiment of the present disclosure.

FIG. 13 is a flowchart showing an example of generating information before motion detection in an embodiment of the present disclosure. Note that in the present embodiment, since the motion detection unit 120 detects a motion actually occurred, information generation before motion detection can be achieved by suppressing information generation during motion detection and after detection, for example. In the example shown in FIG. 13, the motion detection unit 120 executes processing of meal detection (S201) as described above with reference to FIG. 5 and FIG. 6, for example. Here, the information generation unit 130 determines whether a user is during a meal or after a meal (S203). For example, a state in which a user is during a meal may be a state in which sensor data has passed the determination by the pre-filter 122, and further, repetitive and nonperiodic eating motions are being detected by the main analyzer 124. Note that, since it is not necessary to determine whether the user is during a meal or after a meal in this example, the information generation unit 130 can determine that the user is during a meal or after a meal until a predetermined time period (which may correspond to a usual meal interval, for example) elapses after the user once enters the during-meal state.

In a case where it is determined in the above-described determination in S203 that the user is during a meal or after a meal (YES), the information generation unit 130 terminates the process without generating information. On the other hand, in a case where it is determined that the user is not during a meal or not after a meal (NO) (that is, the user is likely to be before a meal), the information generation unit 130 generates recommended information on restaurants (S205 to S209). More specifically, the real-time information generation unit 132 obtains positional information of the user (S205), and generates recommended information on restaurants located close to the user on the basis of the positional information (S207). The positional information of the user may be obtained by the position sensor possessed by the sensor device 100, for example, or may be obtained by a mobile device that serves as the terminal device 200. In addition, when generating recommended information, a publicly-known technology, such as reflecting user preference, for example, can be utilized as necessary. Recommended information on restaurants can be regarded as recommended information concerning the place or contents of a meal. An example of such recommended information will be described further in the following portion with reference to FIG. 14 and FIG. 15. The generated recommended information is output from the output device 140 (S209). As described above, the output device 140 may be, for example, the see-through display 140a possessed by the eye wear 100a, the earphone 140b possessed by the neck wear 100b, the display 140c possessed by the wrist wear 100c, the display 240 possessed by the terminal device 200, or the like in the example shown in FIG. 1, and recommended information is output by an image or sound, for example.

Information as described above may be presented in accordance with, for example, not only whether the user is before a meal, but also whether the user is in a state suitable for receiving information on the basis of another motion recognition result, for example. In this case, for example, in a case where it has been detected (by another motion recognition processing, for example) that the user is still working even before a meal, recommended information on restaurants is not output. Thereafter, when it is detected (by another motion recognition processing, for example) that the user finishes work and has started walking, recommended information on restaurants is generated and presented to the user. Furthermore, in a case where the user has determined a target restaurant and started walking, navigation to the restaurant may be provided.

Figure 14:
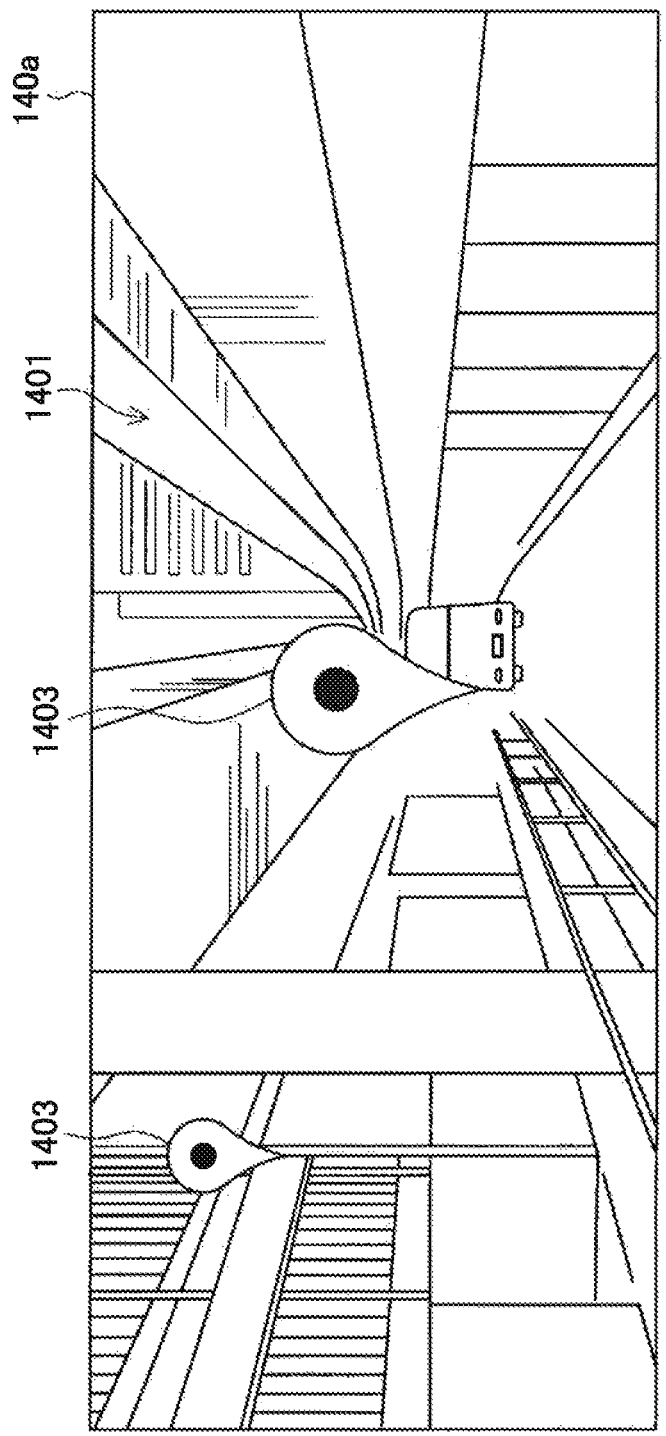
FIG. 14 is an illustration showing a first example of information output in the example shown in FIG. 13.

FIG. 14 is an illustration showing a first example of information output in the example shown in FIG. 13. In the depicted example, recommended information on restaurants is output by the see-through display 140a possessed by the eye wear 100a. An image transparently superimposed on the real-space image 1401 by the see-through display 140a includes icons 1403 indicating the location of the restaurants.

Figure 15:
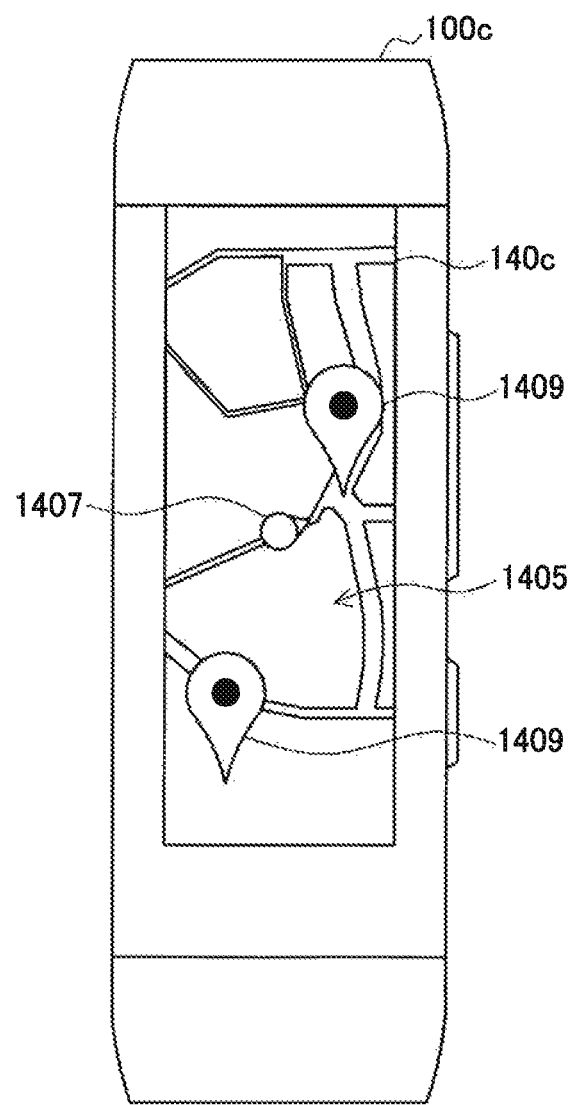
FIG. 15 is an illustration showing a second example of information output in the example shown in FIG. 13.

FIG. 15 is an illustration showing a second example of information output in the example shown in FIG. 13. In the depicted example, recommended information on restaurants is output by the display 140c possessed by the wrist wear 100c. An image displayed on the display 140c includes a map 1405 of the neighborhood of the position of the user and an icon 1407 arranged on the map and indicating the current location, and icons 1409 indicating the location of the restaurants.

In the above-described example, a motion of taking a meal is detected by the motion detection unit 120, and the information generation unit 130 suppresses veneration of recommended information on restaurants after detection of the motion of taking a meal (during a meal and after a meal). In this manner, the example of generating information only before occurrence of a detection target motion may Be effective in a case where, for example, recommended information concerning a motion (in which, for example, a place where the motion is performed and the like are recommended) is generated by the information generation unit 130. By suppressing generation of recommended information in a case where the user has already started the motion (more specifically, recommended information on restaurants is not provided after the user already started a meal or finished a meal, for example), recommended information unnecessary for the user can be prevented from being output.

(5-2. Examples of Generating Information During Motion Detection)

Figure 16:
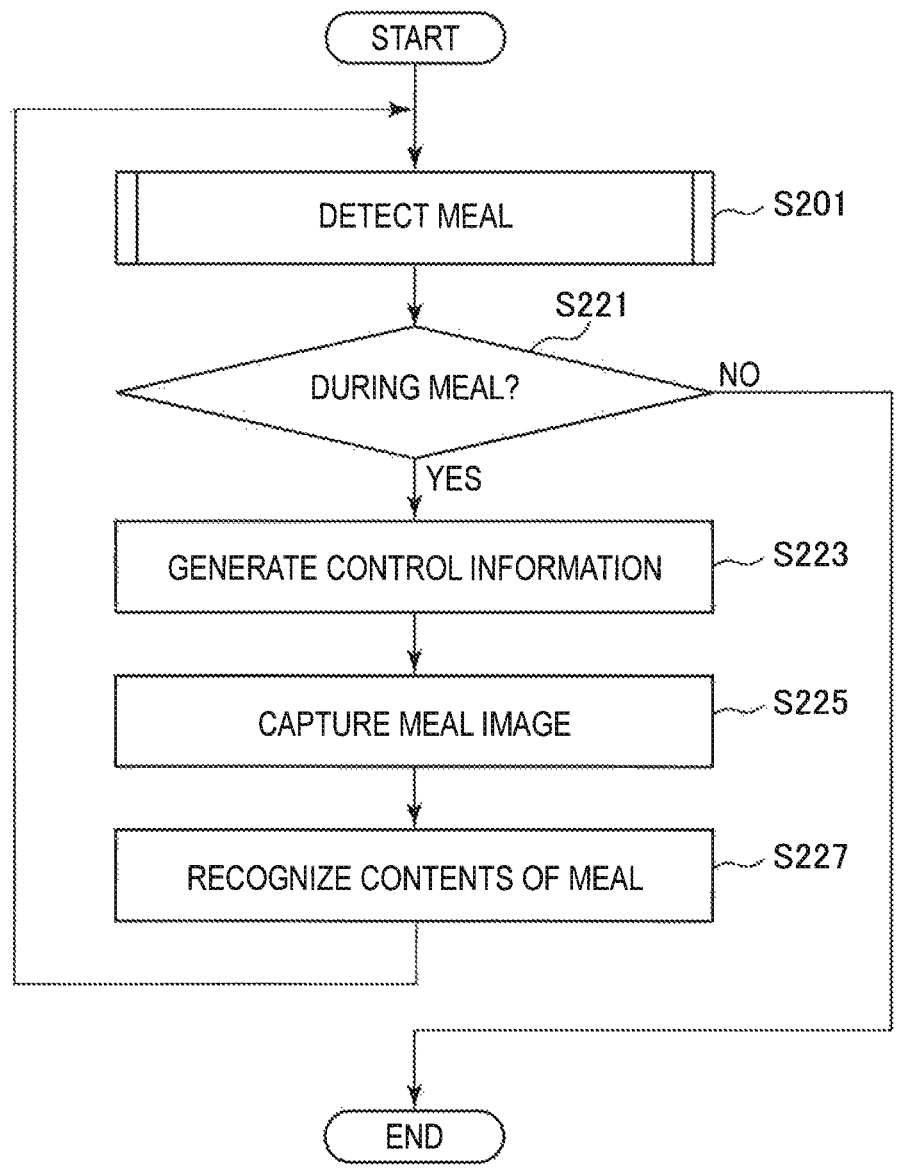
FIG. 16 is a flowchart showing an example of generating information during motion detection in an embodiment of the present disclosure.

FIG. 16 is a flowchart showing an example of generating information during motion detection in an embodiment of the present disclosure. In the example shown in FIG. 16, the motion detection unit 120 executes processing of meal detection (S201) as described above with reference to FIG. 5 and FIG. 6, for example. Here, the information generation unit 130 determines whether a user is during a meal (S221). For example, a state in which the user is during a meal may be a state in which sensor data has passed the determination by the pre-filter 122, and further, repetitive and nonperiodic eating motions are being detected by the main analyzer 124. As described later, this example is aimed at repetitively capturing images of a meal that the user is taking to detect changes. Therefore, in the processing of meal detection in S201 executed repetitively, for example, if an eating motion has been detected even once since a preceding detection, it may be determined that the user is during a meal. Moreover, in a case where failure in detection of an eating motion continues for a predetermined time period in the processing of meal detection in S201 or in a case where sensor data no longer passes the determination by the pre-filter 122, it may be determined that the user is no longer during a meal.

In a case where it is determined that the user is during a meal in the above-described determination in S221 (YES), the real-time information generation unit 132 in the information generation unit 130 generates control information (S223). More specifically, the control information is information for causing a camera that serves as the controlled device 150 in this example to execute image capturing. The camera is an example of a recording device concerning a detected motion. The camera executes capturing of a meal image in accordance with the control information generated in S223 (S225). For the captured meal image, the processor of the terminal device 200 or the server 300, for example, executes processing of image analysis to recognize the contents of the meal (S227). The real-time information generation unit 132 may further generate an advice for the user based on the recognized contents of the meal. The generated information is output as an image, sound, or the like by the output device 140 of various types similarly to the above-described example of FIG. 13. Note that an example of such an advice will be described further in the following portion with reference to FIG. 17 and FIG. 18. For example, in such a case of detecting the order, speed, and the like that the user takes dishes on the basis of a recognition result of the meal image, meal detection (S201) is executed again in a predetermined cycle. Note that such an advice may be directed to the user himself/herself, for example, or may be directed to another person different from the user, for example, parents who manage dietary habits of their child, a caregiver for the elderly, a dietitian, a doctor, or the like.

Figure 17:
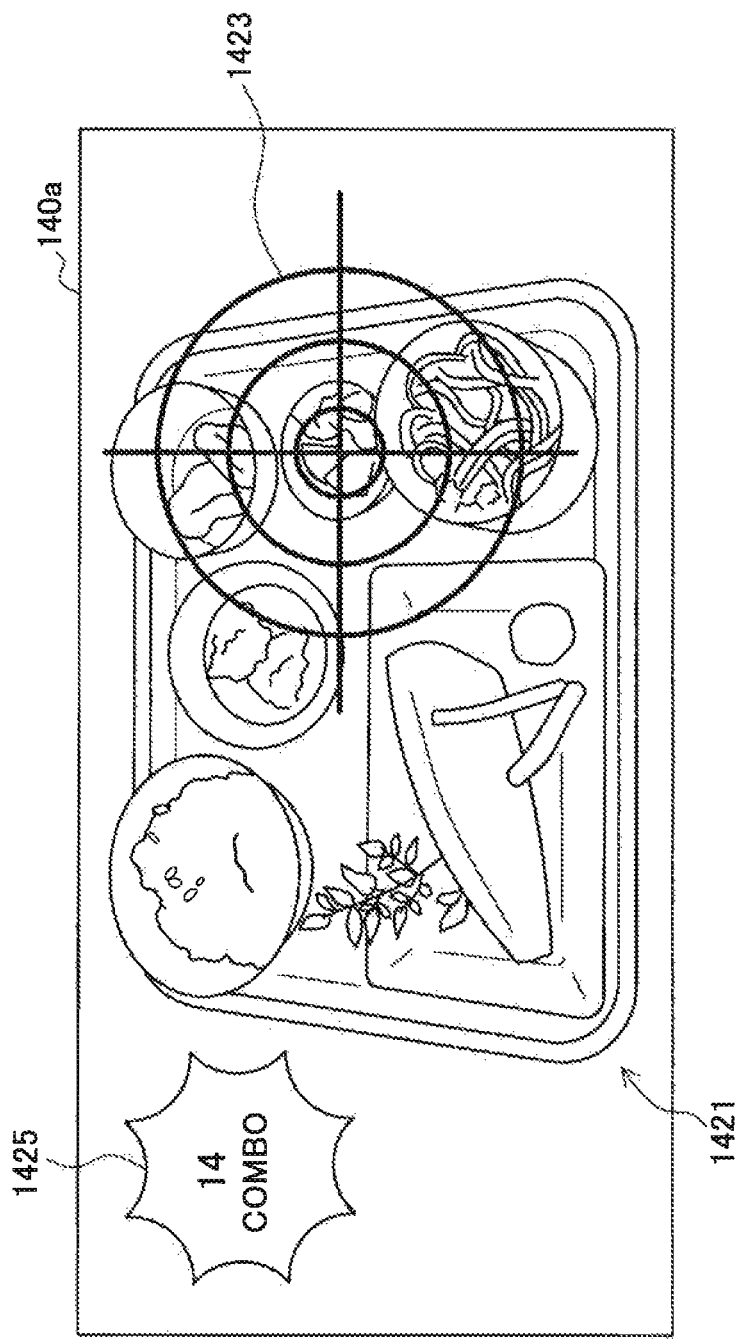
FIG. 17 is an illustration showing a first example of information output in the example shown in FIG. 16.

FIG. 17 is an illustration showing a first example of information output in the example shown in FIG. 16. In the depicted example, information concerning the order that a user takes dishes during a meal is output by the see-through display 140a possessed by the eye wear 100a. An image superimposed on a real-space image 1421 (in the depicted example, including plates of food that the user is taking) by the see-through display 140a includes a target icon 1423 indicating a dish recommended to take next and an indication 1425 of the number of times that the user could have so far continued taking dishes in accordance with recommendation.

Figure 18:
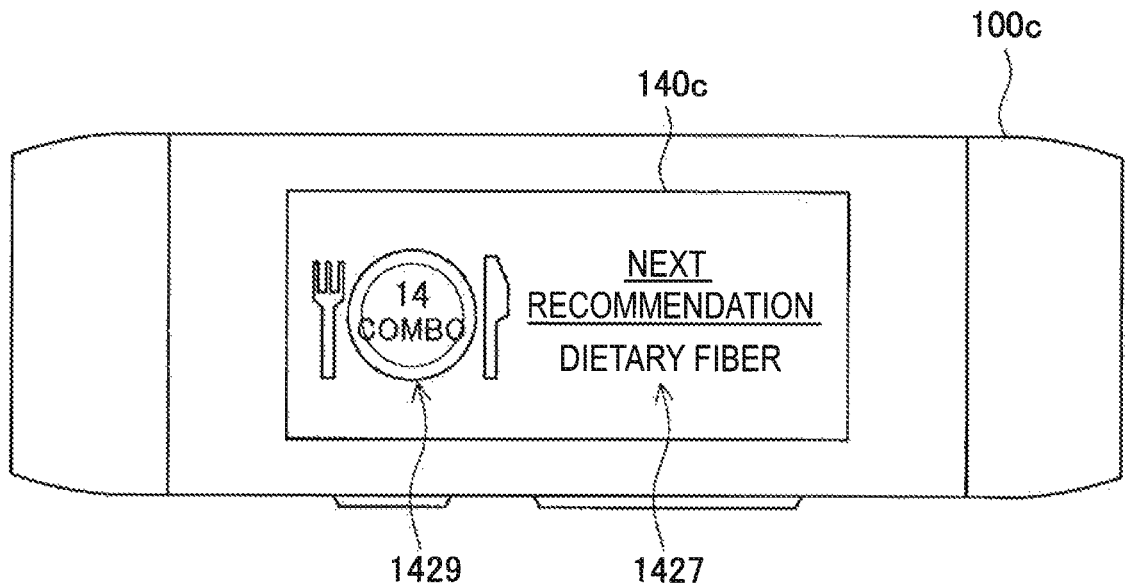
FIG. 18 is an illustration showing a second example of information output in the example shown in FIG. 16.

FIG. 18 is an illustration showing a second example of information output in the example shown in FIG. 16. In the depicted example, information concerning the order that a user takes dishes during a meal is output by the display 140c possessed by the wrist wear 100c. An image displayed on the display 140c includes a target display 1427 showing (the type of) food recommended to take next and an indication 1429 of the number of times that the user could have so far continued taking dishes in accordance with recommendation.

In the above-described example, a motion of taking a meal is detected by the motion detection unit 120, and the information generation unit 130 generates control information for a recording device during detection of the motion of taking a meal (during a meal). Accordingly, the recording device can be operated only during a meal and a meal image can be obtained with a camera, for example. In this case, since image capturing is executed on the premise that the motion of taking a meal has occurred utilizing the detection result of the motion detection unit 120, the possibility that the image is not a meal image can be excluded when analyzing the meal image to recognize the contents of the meal, for example, which can improve the accuracy of recognition and can reduce the processing load. Note that in a case where not only recognition of the contents of a meal, but also recording concerning a motion during motion detection, for example, is to be executed (more specifically, which may be a case of simply recording a motion by an image), the configuration as described above may be effective.

(5-3. Examples of Generating Information after Motion Detection)

Figure 19:
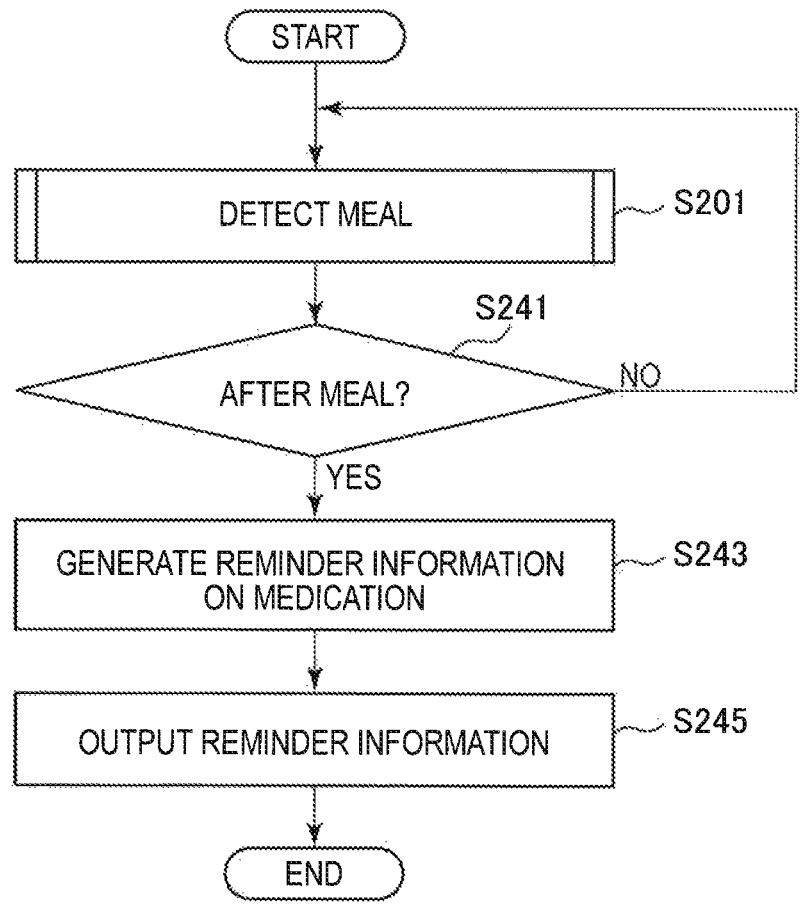
FIG. 19 is a flowchart showing an example of generating information after motion detection in an embodiment of the present disclosure.

FIG. 19 is a flowchart showing an example of generating information after motion detection in an embodiment of the present disclosure. In the example shown in FIG. 19, the motion detection unit 120 executes processing of meal detection (S201) as described above with reference to FIG. 5 and FIG. 6, for example. Here, the information generation unit 130 determines whether a user is after a meal (S241). For example, a state in which the user is after a meal may be a state in which repetitive and nonperiodic eating motions are no longer detected by the main analyzer 124. The information generation unit 130 can determine that the user is after a meal in a case where failure in detection of eating motions continues for a predetermined time period in the processing of meal detection in S201 or in a case where sensor data no longer passes the determination by the pre-filter 122. As described later, this example is aimed at outputting reminder information to a user after a meal. Therefore, in a case where it is determined in S241 that the user is once after a meal and reminder information is generated (S243, S245), it can be determined that the user is before a meal (that is, not after a meal) until a motion of taking a meal (repetitive and nonperiodic eating motions) is detected again thereafter.

In a case where it is determined in the above-described determination in S241 that the user is after a meal (YES), the real-time information generation unit 132 in the information generation unit 130 generates reminder information (S243). In the depicted example, the reminder information is information for reminding a motion scheduled after a meal. A motion to be reminded includes after-meal medication, for example. In this case, a medication schedule recorded by the user may be referred to when generating the reminder information. Moreover, the real-time information generation unit 132 may generate another type of reminder information in a similar manner. For example, the real-time information generation unit 132 may generate reminder information on a plan of the user after the meal referring to the user's schedule. Note that an example of such reminder information will be described further in the following portion with reference to FIG. 20 and FIG. 21. The generated reminder information is output as an image, sound, or the like by the output device 140 of various types (S245) similarly to the above-described example of FIG. 13. On the other hand, in a case where it is determined in the determination in S241 that the user is not after a meal (during a meal or before a meal), meal detection (S201) is executed again in a predetermined cycle.

Figure 20:
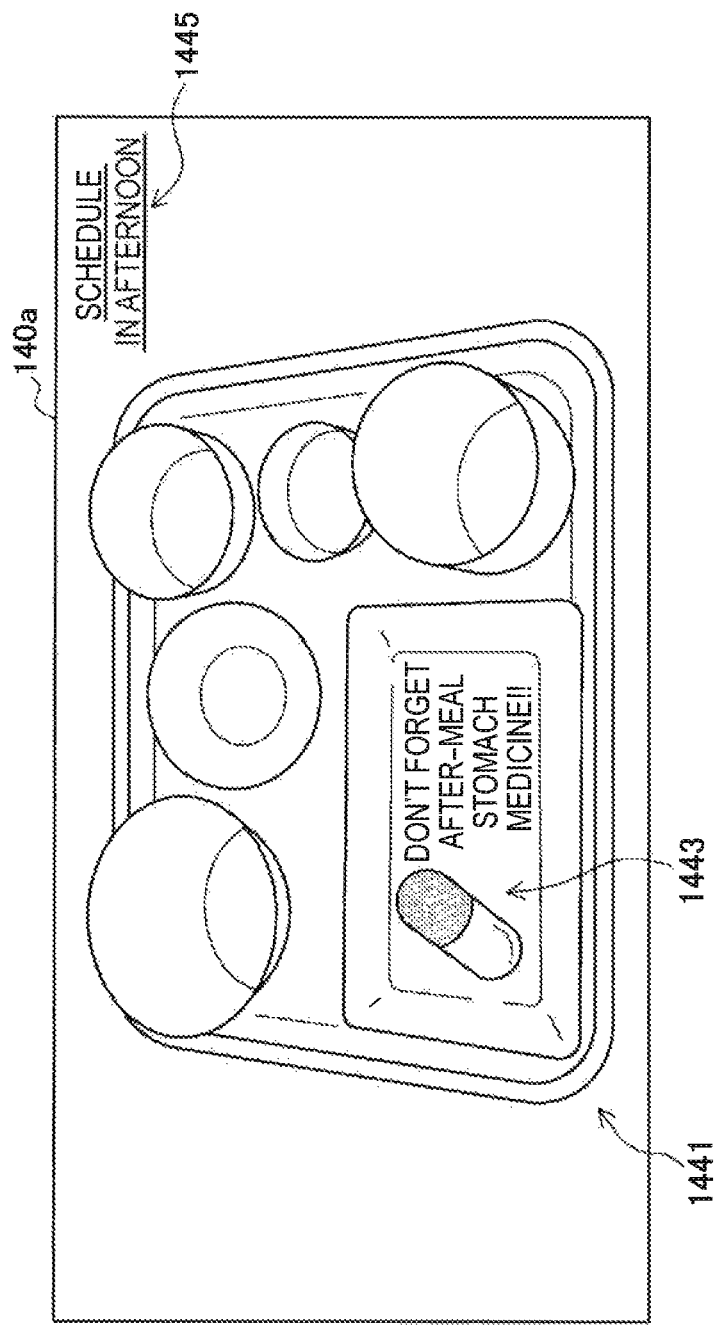
FIG. 20 is an illustration showing a first example of information output in the example shown in FIG. 19.

FIG. 20 is an illustration showing a first example of information output in the example shown in FIG. 19. In the depicted example, reminder information is output by the see-through display 140a possessed by the eye wear 100a. An image superimposed on a real-space image 1441 (in the depicted example, including plates of food that a user has finished) by the see-through display 140a includes reminder information 1443 on after-meal medication (stomach medicine) and a link 1445 to reminder information on an after-meal plan of the user.

Figures 21, 22:
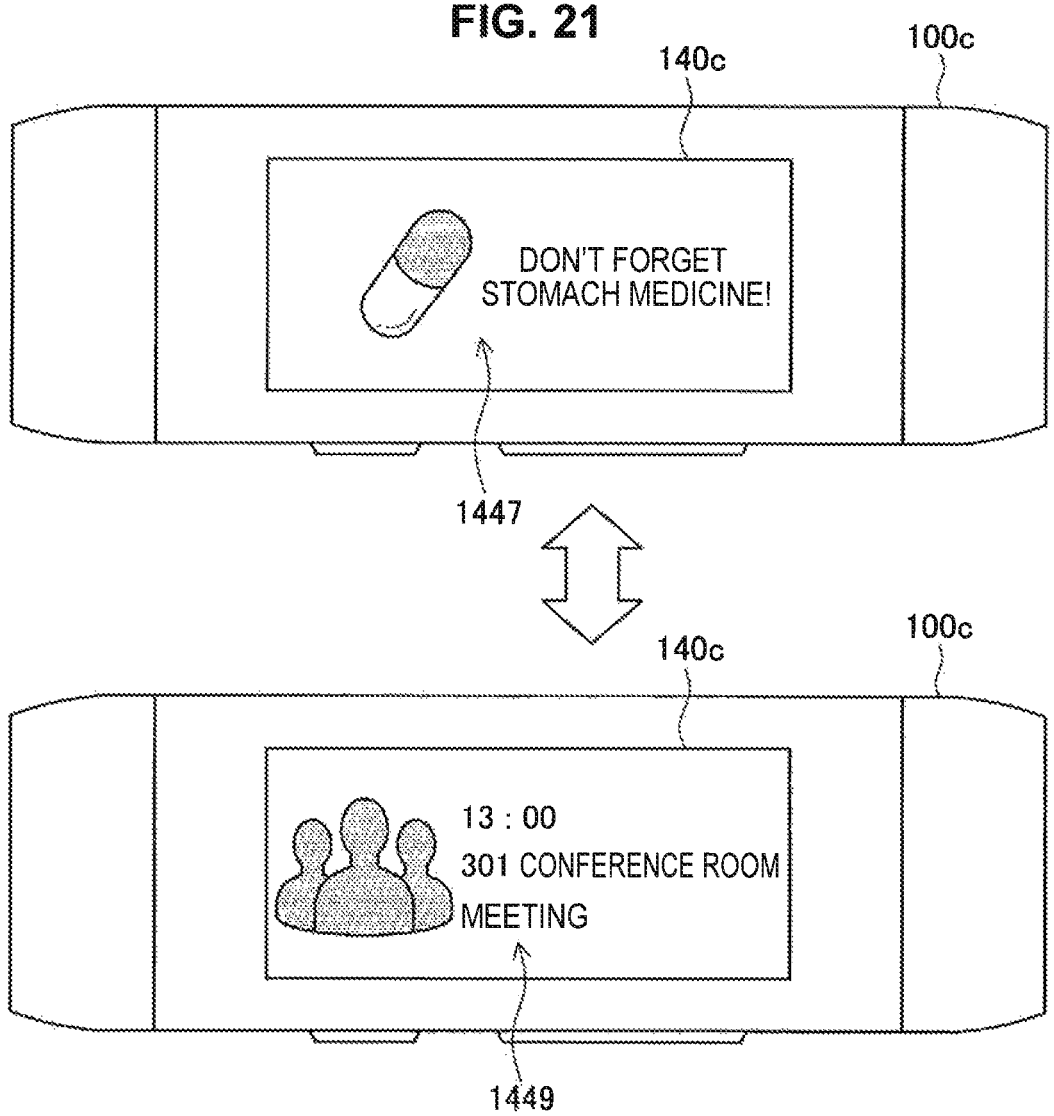
FIG. 21 is an illustration showing a second example of information output in the example shown in FIG. 19.
FIG. 22 is an illustration showing variations of information that may be provided in the case of detecting a motion of taking a meal in an embodiment of the present disclosure.

FIG. 21 is an illustration showing a second example of information output in the example shown in FIG. 19. In the depicted example, reminder information 1447 on after-meal medication (stomach medicine) and reminder information 1449 on an after-meal plan of the user are output alternately by the display 140c possessed by the wrist wear 100c.

In the above-described example, a motion of taking a meal is detected by the motion detection unit 120, and the information generation unit 130 generates reminder information after detection of the motion of taking a meal. In this manner, the example of generating information after occurrence of a detection target motion may be effective in such a case where, for example, there is another motion for which an before-after relation with a detection target motion has been specified (in the above-described example, a motion of medication with respect to a meal). With information output for the first time after the user finishes a motion (for example, taking a meal), information such as a reminder is provided at the timing effective for the user.

Note that in the examples having been described so far, solely the real-time information generation unit 132 generates information, whilst the log generation unit 134 may generate various types of information as already described. More specifically, for example, the log generation unit 134 may generate a log of a time slot of a meal or the contents of the meal. In this case, a section in which detection of an eating motion has continued repetitively and nonperiodically can be specified later as a mealtime section. Moreover, the contents of a meal may be detected utilizing a meal image captured during detection of a motion of taking a meal, as in the example described above with reference to FIG. 16. Furthermore, for example, the log generation unit 134 may detect the amount of conversation in a mealtime section utilizing a microphone possessed by the sensor device 100 or the like and record the amount as an index of livening-up of a conversation. In addition, the log generation unit 134 may record the magnitude of gestures (motions other than taking a meal) detected along with a meal (for example, during eating motions) as an index of the degree of livening-up of a conversation. Furthermore, for example, the log generation unit 134 may detect environmental sound, voice of the user's own, and the like from sound detected by the microphone to presume whether the place of a meal is a formal place or a casual place.

In addition, the log generation unit 134 may generate a log that expresses an index concerning a motion of taking a meal or the like as described above, for example, by a relative value, not an absolute value. For example, a meal may be expressed depending on whether it is longer or shorter than usual, not by a specific time period (30 minutes, etc.). Moreover, for example, the index of livening-up of a conversation may express whether it was liven up or not liven up as compared with the average of a population to which the user belongs (for example, Japanese males in thirties, etc.). Such a relative expression can be made by storing a dictionary of statistics concerning index values in a storage of the terminal device 200 or the server 300, for example.

(5-4. Other Examples)

FIG. 22 to FIG. 24 are illustrations showing variations of information that may be provided before motion detection (before a meal), during detection (during a meal), after detection (after a meal) in the case of detecting a motion of taking a meal in an embodiment of the present disclosure. In the embodiment of the present disclosure, various contents of information can also be generated similarly in a case of detecting a motion other than taking a meal, for example. In addition, the case of detecting a meal is not limited to the depicted contents, but also various types of information effective for a user can be generated.

In the before-meal example shown in FIG. 22, in a case of taking a meal at home, for example, information of the contents of shopping, cooking, preparation, and the like can be generated. Preparation includes hand washing before a meal, for example. In a case of taking a meal at a restaurant or taking a delivered meal, information of the contents, such as menu display, menu selection, and order can be generated. In a case of menu display, recommendation from a restaurant or the like may be displayed, or a food combination instruction or a warning on dietary restrictions may be output for a menu which is going to be selected. Moreover, in a case of menu selection, data concerning user's meals in the past may be displayed.

In the during-meal example shown in FIG. 23, information that recommends the timing for serving a meal, for example, can be generated. In addition, an instruction to prevent overeating, an instruction to keep the eating speed within a proper range, an instruction on the order of eating, an instruction on the manner, and the like can be performed while an eating motion is occurring. In a case where it is detected that the user is during a meal while doing something (for example, while watching television, while listening to music, while reading a newspaper, or while working), information concerning such contents (television, music, newspaper, work, etc.) may be generated upon consideration that the user is during a meal.

Furthermore, in the during-meal example, information presentation that makes a meal enjoyable while the user is taking a meal with another user can also be performed. More specifically, a topic of conversation, for example, can be provided, information concerning the contents of conversation can be presented, or information on the partner who is taking a meal together can be presented. Alternatively, such information that makes a meal delicious may be presented. More specifically, information on the contents of a meal, for example, information on the production area of food materials, characteristics of food materials, a bit of knowledge concerning cooking, recommended food combination menu, and the like may be presented. Alternatively, information on the place where a meal is being taken, for example, the history or topic of a restaurant where a meal is being taken, a popular menu, information on the surrounding area of a restaurant, or the like may be provided. Note that in the case where the user is taking a meal with another user, control may be exerted such that, in consideration of privacy, information, such as a food combination instruction, a warning on dietary restrictions, data concerning meals in the past, and the like, for example, is not output, or not output in such a manner that the information will be recognized by the other user.

In the after-meal example shown in FIG. 24, in a case where a user has means for disseminating comments on a meal, for example, a link to a blog or a review site may be displayed, or sharing of comments at a social media may be prompted. Moreover, from the viewpoint of dietary management, information on a meal contents instruction in view of the contents of a meal having been taken may be presented. At this time, a caloric intake or a nutrition intake may be calculated. Furthermore, from the viewpoint of health management, information on an exercise instruction in view of the contents of a meal having been taken may be presented. At this time, caloric consumption by an exercise may be calculated and compared with a caloric intake in the meal. In addition, as in the above-described example, an alarm for preventing failure to take a medicine may be provided. Alternatively, information presentation concerning an after-meal action may be carried out. In this case, for example, information presentation in line with the user's schedule or a To Do list may be performed. Moreover, in a case where the user has nothing special to do or the user is taking a break, information on entertainment may be presented. Furthermore, at a timing of presenting some information on the basis of finishing a meal, another action log (for example, a log generated by another action recognition processing) may be used. For example, in a case where a snack is detected in the afternoon, and additionally, where overeating is detected, information presentation, such as prompting walking when the user starts going home after the end of the snack, or issuing an alert to stop taking a snack when the user is directed to a convenience store next day, may be executed.

(6. Hardware Configuration)

Figure 25:
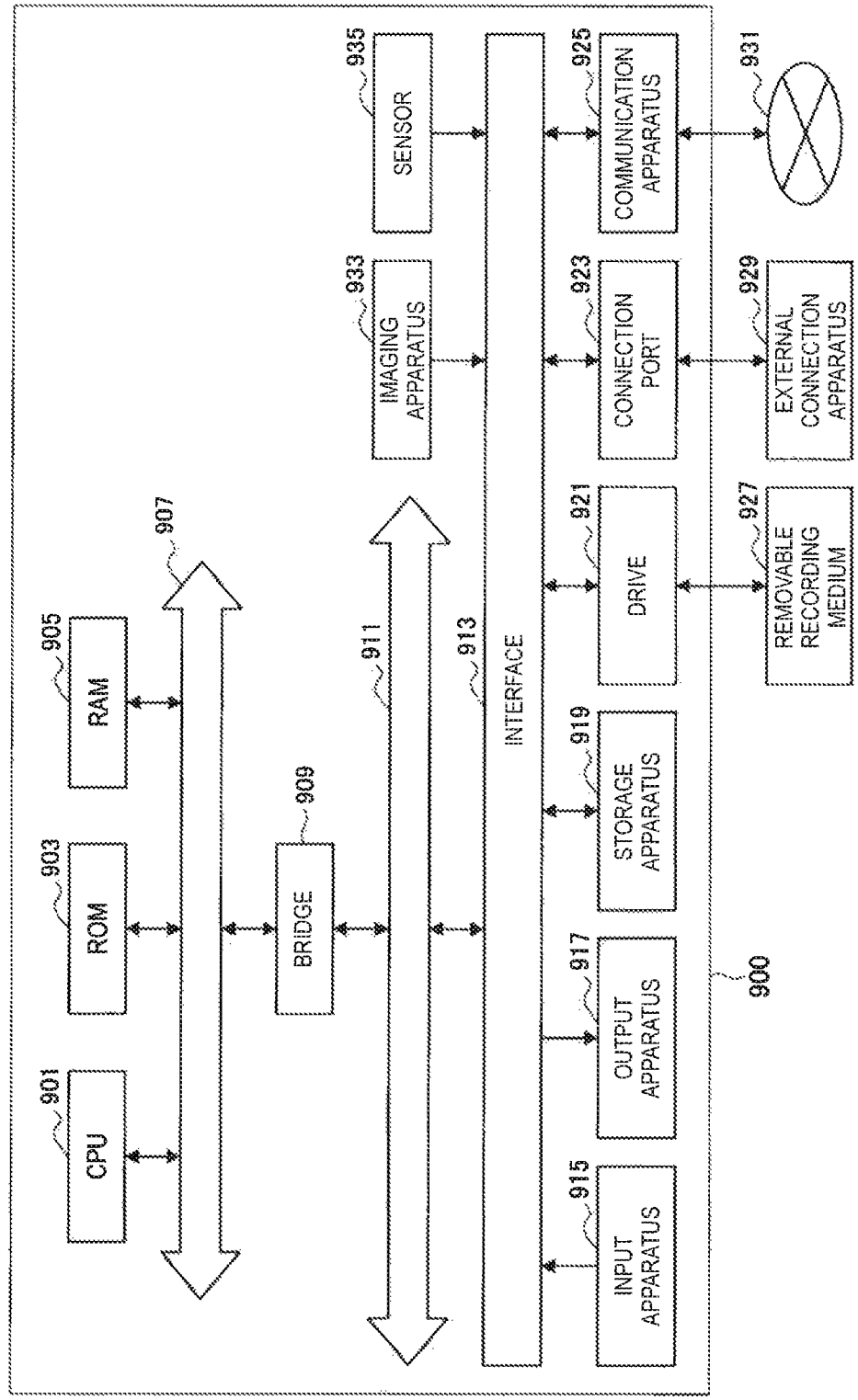
FIG. 25 is a block diagram showing a hardware configuration example of an information processing apparatus according to an embodiment of the present disclosure.

Next, with reference to FIG. 25, a hardware configuration of an information processing apparatus according to an embodiment of the present disclosure is explained. FIG. 25 is a block diagram illustrating a hardware configuration example of an information processing apparatus according to the embodiment of the present disclosure, A depicted information processing apparatus 900 may implement the sensor device, the terminal device, and/or the server in the above-described embodiment, for example.

The information processing apparatus 900 includes a central processing unit (CPU) 901, read only memory (ROM) 903, and random access memory (RAM) 905. In addition, the information processing apparatus 900 may include a host bus 907, a bridge 909, an external bus 911, an interface 913, an input apparatus 915, an output apparatus 917, a storage apparatus 919, a drive 921, a connection port 923, and a communication apparatus 925. Moreover, the information processing apparatus 900 may include an imaging apparatus 933, and a sensor 935, as necessary. The information processing apparatus 900 may include a processing circuit such as a digital signal processor (DSP), an application-specific integrated circuit (ASIC), or a field-programmable gate array (FPGA), alternatively or in addition to the CPU 901.

The CPU 901 serves as an arithmetic processing apparatus and a control apparatus, and controls the overall operation or a part of the operation of the information processing apparatus 900 according to various programs recorded in the ROM 903, the RAM 905, the storage apparatus 919, or a removable recording medium 927. The ROM 903 stores programs, operation parameters, and the like used by the CPU 901. The RAM 905 transiently stores programs used when the CPU 901 is executed, and various parameters that change as appropriate when executing such programs. The CPU 901, the ROM 903, and the RAM 905 are connected with each other via the host bus 907 configured from an internal bus such as a CPU bus or the like. The host bus 907 is connected to the external bus 911 such as a Peripheral Component Interconnect/Interface (PCI) bus via the bridge 909.

The input apparatus 915 is a device operated by a user such as a mouse, a keyboard, a touch panel, a button, a switch, and a lever. The input apparatus 915 may be a remote control device that uses, for example, infrared radiation and another type of radiowave. Alternatively, the input apparatus 915 may be an external connection apparatus 929 such as a mobile phone that corresponds to an operation of the information processing apparatus 900. The input apparatus 915 includes an input control circuit that generates input signals on the basis of information which is input by a user to output the generated input signals to the CPU 901. A user inputs various types of data to the information processing apparatus 900 and instructs the information processing apparatus 900 to perform a processing operation by operating the input apparatus 915.

The output apparatus 917 includes an apparatus that can report acquired information to a user visually, audibly, or haptically. The output apparatus 917 may be, for example, a display device such as a liquid crystal display (LCD) or an organic electro-luminescence (EL) display, an audio output apparatus such as a speaker or a headphone, or a vibrator. The output apparatus 917 outputs a result obtained through a process performed by the information processing apparatus 900, in the form of video such as text and an image, sounds such as voice and audio sounds, or vibration.

The storage apparatus 919 is an apparatus for data storage that is an example of a storage unit of the information processing apparatus 900. The storage apparatus 919 includes, for example, a magnetic storage device such as a hard disk drive (HDD), a semiconductor storage device, an optical storage device, or a magneto-optical storage device. The storage apparatus 919 stores therein the programs and various data executed by the CPU 901, various data acquired from an outside, and the like.

The drive 921 is a reader/writer for the removable recording medium 927 such as a magnetic disk, an optical disc, a magneto-optical disk, and a semiconductor memory, and built in or externally attached to the information processing apparatus 900. The drive 921 reads out information recorded on the mounted removable recording medium 927, and outputs the information to the RAM 905. The drive 921 writes the record into the mounted removable recording medium 927.

The connection port 923 is a port used to connect devices to the information processing apparatus 900. The connection port 923 may include a Universal Serial Bus (USB) port, an IEEE1394 port, and a Small Computer System Interface (SCSI) port. The connection port 923 may further include an RS-232C port, an optical audio terminal, a High-Definition Multimedia Interface (HDMI) (registered trademark) port, and so on. The connection of the external connection apparatus 929 to the connection port 923 makes it possible to exchange various data between the information processing apparatus 900 and the external connection apparatus 929.

The communication apparatus 925 is a communication interface including, for example, a communication device for connection to a communication network 931. The communication apparatus 925 may be, for example, a communication card for a local area network (LAN), Bluetooth (registered trademark), Wi-Fi, or a wireless USB (WISH). The communication apparatus 925 may also be, for example, a router for optical communication, a router for asymmetric digital subscriber line (ADSL), or a modem for various types of communication. For example, the communication apparatus 925 transmits and receives signals in the Internet or transits Signals to and receives signals from another communication device by using a predetermined protocol such as TCP/IP. The communication network 931 to which the communication apparatus 925 connects is a network established through wired or wireless connection. The communication network 931 may include, for example, the Internet, a home LAN, infrared communication, radio communication, or satellite communication.

The imaging apparatus 933 is an apparatus that captures an image of a real space by using an image sensor such as a charge coupled device (CCD) and a complementary metal oxide semiconductor (CMOS), and various members such as a lens for controlling image formation of a subject image onto the image sensor, and generates the captured image. The imaging apparatus 933 may capture a still image or a moving image.

The sensor 935 is various sensors such as an acceleration sensor, an angular velocity sensor, a geomagnetic sensor, an illuminance sensor, a temperature sensor, a barometric sensor, and a sound sensor (microphone). The sensor 935 acquires information regarding a state of the information processing apparatus 900 such as a posture of a housing of the information processing apparatus 900, and information regarding an environment surrounding the information processing apparatus 900 such as luminous intensity and noise around the information processing apparatus 900. The sensor 935 may include a global positioning system (GPS) receiver that receives GPS signals to measure latitude, longitude, and altitude of the apparatus.

The example of the hardware configuration of the information processing apparatus 900 has been described. Each of the structural elements described above may be configured by using a general purpose component or may be configured by hardware specialized for the function of each of the structural elements. The configuration may be changed as necessary in accordance with the state of the art at the time of working of the present disclosure.

(7. Supplement)

The embodiments of the present disclosure may include, for example, the above-described information processing apparatus (the sensor device, the terminal device, and/or the server), the above-described system, the information processing method executed by the information processing apparatus or the system, a program for causing the information processing apparatus to exhibits its function, and a non-transitory physical medium having the program stored therein.

The preferred embodiment(s) of the present disclosure has/have been described above with reference to the accompanying drawings, whilst the present disclosure is not limited to the above examples. A person skilled in the art may find various alterations and modifications within the scope of the appended claims, and it should be understood that they will naturally come under the technical scope of the present disclosure.

Further, the effects described in this specification are merely illustrative or exemplified effects, and are not limitative. That is, with or in the place of the above effects, the technology according to the present disclosure may achieve other effects that are clear to those skilled in the art from the description of this specification.

Additionally, the present technology may also be configured as below.

(1)

An information processing apparatus including:
  a motion detection unit configured to detect a series of motions of a user which are repetitive and nonperiodic; and
  an information generation unit configured to generate information related to the series of motions.

(2)

The information processing apparatus according to (1), in which
  the motion detection unit detects the series of motions on the basis of a plurality of pieces of sensor data different in sensing target or sensing method.

(3)
The information processing apparatus according to (2), in which
the plurality of pieces of sensor data include first sensor data and second sensor data, and
the motion detection unit includes
a first motion detection unit configured to determine whether a section in which the first sensor data satisfies a first condition corresponding to the series of motions has occurred, and
a second motion detection unit configured to, in a case where it is determined that the section in which the first condition is satisfied has occurred, determine whether the second sensor data satisfies a second condition corresponding to the series of motions in the section.

(4)
The information processing apparatus according to (2), in which
the plurality of pieces of sensor data include first sensor data and second sensor data obtained in an external sensor device,
the information processing apparatus further includes a receiving unit configured to, in a case where it is determined in the sensor device that a section in which the first sensor data satisfies a first condition corresponding to the series of motions has occurred, receive the second sensor data transmitted from the sensor device, and
the motion detection unit determines whether the second sensor data satisfies a second condition corresponding to the series of motions in the section in which the first condition is satisfied.

(5)
The information processing apparatus according to any one of (1) to (4), in which
the information includes information generated in accordance with an before-after relation with detection of the series of motions.

(6)
The information processing apparatus according to (5), in which
the information includes first information generated during detection of the series of motions.

(7)
The information processing apparatus according to (6), in which
the first information includes control information for a recording device concerning the series of motions.

(8)
The information processing apparatus according to (7), in which
the series of motions correspond to a meal, and
the recording device records contents of the meal by an image in accordance with the control information.

(9)
The information processing apparatus according to (8), in which
the first information further includes an advice for the user or an advice for another person different from the user based on the contents of the meal.

(10)
The information processing apparatus according to any one of (5) to (9), in which
the information is generated in accordance with the before-after relation with detection of the series of motions and a result of recognition of an action of the user different from the series of motions.

(11)
The information processing apparatus according to any one of (5) to (10), in which
the information includes second information generated after detection of the series of motions.

(12)
The information processing apparatus according to (11), in which
the second information includes reminder information on a motion scheduled after the series of motions.

(13)
The information processing apparatus according to any one of (5) to (12), in which
the information includes third information, generation of which is suppressed during detection and after detection of the series of motions.

(14)
The information processing apparatus according to (13), in which
the third information includes recommended information concerning the series of motions.

(15)
The information processing apparatus according to (14), in which
the series of motions correspond to a meal, and
the recommended information includes recommended information concerning a place or contents of the meal.

(16)
The information processing apparatus according to any one of (1) to (15), in which
the information includes log information generated after detection of the series of motions.

(17)
The information processing apparatus according to (16), in which
the information further includes control information for a recording device concerning the series of motions, the control information being generated during detection of the series of motions, and
the log information includes a record concerning the series of motions recorded by the recording device in accordance with the control information.

(18)
The information processing apparatus according to (17), in which
the series of motions correspond to a meal,
the recording device records contents of the meal by images, and
the log information includes a time slot of the meal and at least one of the images recorded in the time slot of the meal.

(19)
An information processing method including:
detecting, by a processor, a series of motions of a user which are repetitive and nonperiodic; and
generating information related to the series of motions.

(20)
A program for causing a computer to achieve:
a function of detecting a series of motions of a user which are repetitive and nonperiodic; and
a function of generating information related to the series of motions.

REFERENCE SIGNS LIST

10 system
100 sensor device 110 sensor
112 single-axis acceleration
114 three-axis acceleration
120, 220 motion detection unit
122 pre-filter
124 main analyzer
130 information generation unit
132 real-time information generation unit
134 log generation unit
140, 240 output device
150, 250 controlled device
160, 260 database
170 sensor control unit
180 transmission unit
210 receiving unit
300 server

The invention claimed is:

1. An information processing apparatus comprising:
a motion detection unit configured to detect, based on image data including repetitively captured images obtained by an image sensor, a target motion that is characterized as a series of motions of a user which are repetitive and nonperiodic; and
an information generation unit configured to generate information related to the series of motions and including a reminder information prompting for performance of a new activity after completion by the user of an activity that is associated with the target motion,
wherein the motion detection unit detects the series of motions of the user based on detected changes between the repetitively captured images, and
wherein the motion detection unit and the information generation unit are each implemented via at least one processor.

2. The information processing apparatus according to claim 1, wherein
the motion detection unit detects the series of motions on the basis of a plurality of pieces of sensor data including data associated with different sensing targets or sensing methods.

3. The information processing apparatus according to claim 2, wherein
the plurality of pieces of sensor data include first sensor data and second sensor data, and
the motion detection unit includes
a first motion detection unit configured to determine whether a section in which the first sensor data satisfies a first condition corresponding to the series of motions has occurred, and
a second motion detection unit configured to, in a case where it is determined that the section in which the first condition is satisfied has occurred, determine whether the second sensor data satisfies a second condition corresponding to the series of motions in the section.

4. The information processing apparatus according to claim 2, wherein
the plurality of pieces of sensor data include first sensor data and second sensor data obtained in an external sensor device,
the information processing apparatus further comprises a receiving unit configured to, in a case where it is determined in the external sensor device that a section in which the first sensor data satisfies a first condition corresponding to the series of motions has occurred, receive the second sensor data transmitted from the external sensor device, and the motion detection unit determines whether the second sensor data satisfies a second condition corresponding to the series of motions in the section in which the first condition is satisfied.

5. The information processing apparatus according to claim 1, wherein
the information includes information generated in accordance with a before-after relation with detection of the series of motions.

6. The information processing apparatus according to claim 5, wherein
the information includes first information generated during detection of the series of motions.

7. The information processing apparatus according to claim 6, wherein
the first information includes control information for a recording device concerning the series of motions.

8. The information processing apparatus according to claim 7, wherein
the series of motions correspond to a meal, and
the recording device records contents of the meal by an image in accordance with the control information.

9. The information processing apparatus according to claim 8, wherein
the first information further includes an advice for the user or an advice for another person different from the user based on the contents of the meal.

10. The information processing apparatus according to claim 5, wherein
the information is generated in accordance with the before-after relation with detection of the series of motions and a result of recognition of an action of the user different from the series of motions.

11. The information processing apparatus according to claim 5, wherein
the information includes second information generated after detection of the series of motions.

12. The information processing apparatus according to claim 11, wherein
the second information includes the reminder information on a motion associated with the new activity and scheduled after the series of motions.

13. The information processing apparatus according to claim 5, wherein the information includes third information, generation of which is suppressed during detection and after detection of the series of motions.

14. The information processing apparatus according to claim 13, wherein
the third information includes recommended information concerning the series of motions.

15. The information processing apparatus according to claim 14, wherein
the series of motions correspond to a meal, and
the recommended information includes recommended information concerning a place or contents of the meal.

16. The information processing apparatus according to claim 1, wherein
the information includes log information generated after detection of the series of motions.

17. The information processing apparatus according to claim 16, wherein
the information further includes control information for a recording device concerning the series of motions, the control information being generated during detection of the series of motions, and the log information includes a record concerning the series of motions recorded by the recording device in accordance with the control information.

18. The information processing apparatus according to claim 17, wherein
the series of motions correspond to a meal,
the recording device records contents of the meal by images, and
the log information includes a time slot of the meal and at least one of the images recorded in the time slot of the meal.

19. An information processing method comprising:
detecting, by a processor and based on image data including repetitively captured images obtained by an image sensor, a target motion that is characterized as a series of motions of a user which are repetitive and nonperiodic; and
generating information related to the series of motions and including a reminder information prompting for performance of a new activity after completion by the user of an activity that is associated with the target motion,
wherein the series of motions of the user are detected based on detected changes between the repetitively captured images.

20. A non-transitory computer-readable medium having embodied thereon a program, which when executed by a computer causes the computer to execute a method, the method comprising:
detecting, based on image data including repetitively captured images obtained by an image sensor, a target motion that is characterized as a series of motions of a user which are repetitive and nonperiodic; and
generating information related to the series of motions and including a reminder information prompting for performance of a new activity after completion by the user of an activity that is associated with the target motion,
wherein the series of motions of the user are detected based on detected changes between the repetitively captured images.

* * * * *